United States Patent
Ward

(10) Patent No.: US 6,296,654 B1
(45) Date of Patent: Oct. 2, 2001

(54) NON-INVASIVE AORTIC IMPINGEMENT

(75) Inventor: Kevin R Ward, Glen Allen, VA (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 09/446,288

(22) PCT Filed: Jun. 24, 1998

(86) PCT No.: PCT/US98/13109

§ 371 Date: Apr. 28, 2000

§ 102(e) Date: Apr. 28, 2000

(87) PCT Pub. No.: WO99/00057

PCT Pub. Date: Jan. 7, 1999

Related U.S. Application Data

(60) Provisional application No. 60/050,133, filed on Jun. 27, 1997.

(51) Int. Cl.[7] .................................................. A61M 25/10
(52) U.S. Cl. ............................ 606/192; 128/898; 600/207
(58) Field of Search ........................ 600/16, 18, 207; 606/192; 607/105; 128/898

(56) References Cited

U.S. PATENT DOCUMENTS

| | | |
|---|---|---|
| 3,425,419 | 2/1969 | Dato ................................. 607/106 |
| 4,090,518 | 5/1978 | Elam . |
| 4,198,963 | 4/1980 | Barkalow et al. . |
| 4,640,298 | 2/1987 | Pless et al. . |
| 4,706,688 | 11/1987 | Don Michael et al. . |
| 4,960,133 | 10/1990 | Hewson . |
| 5,056,532 | 10/1991 | Hull et al. . |
| 5,077,667 | 12/1991 | Brown et al. . |
| 5,151,100 | 9/1992 | Abele et al. ........................ 607/113 |
| 5,170,803 | 12/1992 | Hewson et al. . |
| 5,179,952 | 1/1993 | Buinevicius et al. . |
| 5,188,602 | 2/1993 | Nichols ............................. 607/105 |
| 5,191,885 | 3/1993 | Bilof et al. . |
| 5,197,491 | 3/1993 | Anderson et al. . |
| 5,261,411 | 11/1993 | Hughes ............................. 128/898 |
| 5,387,232 | 2/1995 | Trailer ............................... 607/124 |
| 5,398,692 | 3/1995 | Hickey .............................. 128/673 |
| 5,423,807 | 6/1995 | Milder .............................. 607/105 |
| 5,431,696 | 7/1995 | Atlee, III .......................... 128/642 |
| 5,437,633 | 8/1995 | Manning .......................... 128/898 |
| 5,486,208 | 1/1996 | Ginsburg .......................... 607/106 |
| 5,531,776 | 7/1996 | Ward et al. ....................... 607/105 |
| 5,556,425 | 9/1996 | Hewson et al. ................... 607/124 |
| 5,716,386 | 2/1998 | Ward et al. ....................... 607/106 |

OTHER PUBLICATIONS

Product brochure entitled "EsoThor™ —Esophageal—Thoracic Technology Min–Invasive A–V Sequential Pacing," published by Brunswick Biomedical Technologies, date unknown.

Brown, Charles G., M.D. et al., "A Comparison of Standard–Dose and High–Dose Epinephrine in Cardiac Arrest Outside the Hospital," *New England Journal of Medicine*, vol. 327, Oct. 8, 1992, pp. 1051–1055.

(List continued on next page.)

*Primary Examiner*—Michael H. Thaler
(74) *Attorney, Agent, or Firm*—Van Dyke, Gardner, Linn & Burkhart, LLP

(57) ABSTRACT

A method for subdiaphragm hemorrhage control in a patient or for non-invasively enhancing cerebral and myocardial perfusion in a patient includes positioning a moveable surface through the esophagus adjacent the patient's esophageal-gastric junction and displacing the moveable surface thereby applying a force posteriorly in the direction of the patient's descending aorta sufficient to partially or substantially completely occlude the descending aorta. The moveable surface may be positionable in a lower portion of the esophagus where the esophagus and the aorta pass through the diaphragm or may be positioned in a portion of the patient's stomach juxtaposed with the patient's descending aorta.

51 Claims, 29 Drawing Sheets

OTHER PUBLICATIONS

Manning, James E., M.D. et al., "Selective Aortic Arch Perfusion During Cardiac Arrest: A New Resuscitation Technique," *Annals of Emergency Medicine*, Sep., 1992, pp. 1058–1065.

Berg, Robert A., M.D., F.A.A.P. et al., "High–Dose Epinephrine Results in Greater Early Mortality After Resuscitation From Prolonged Cardiac Arrest in Pigs: A Prospective, Randomized Study," *Critical Care Medicine*, vol. 22, No. 2, Feb., 1994, pp. 282–290.

Mattox, Kenneth L., M.D. et al., "Prospective MAST Study in 911 Patients," *The Journal of Trauma*, vol. 29, No. 8, Aug., 1989, pp. 1104–1112.

Eisenberg, Mickey S., M.D., PhD et al., "Cardiac Arrest and Resuscitation: A Tale of 29 Cities," *Annals of Emergency Medicine*, Feb., 1990, pp. 179–186.

Eisenberg, Mickey S., M.D., PhD et al., "Long–Term Survival After Out–of Hospital Cardiac Arrest," *The New England Journal of Medicine*, vol. 306, No. 22, Jun. 3, 1982, pp. 1340–1343.

Becker, Lance B., M.D. et al., "Outcome of CPR in a Large Metropolitan Area—Where are the Survivors?," *Annals of Emergency Medicine*, Apr., 1991, pp. 355–361.

Safar, Peter, M.D., "Resuscitation From Clinical Death: Pathophysiologic Limits and Therapeutic Potentials," *Critical Care Medicine*, vol. 16, No. 10, Oct., 1988, pp. 923–941.

Safar, Peter, M.D., "Cerebral Resuscitation After Cardiac Arrest: Research Initiatives and Future Directions," *Annals of Emergency Medicine*, Feb., 1993, pp. 324–349.

Wolfson, Jr., Sidney K. et al., "Dynamic Heterogeneity of Cerebral Hypoperfusion After Prolonged Cardiac Arrest in Dogs Measured by the Stable Xenon/CT Technique: A Preliminary Study," *Resuscitation*, 23 (1992), pp. 1–20.

Brown, Charles G., M.D. et al., "The Effect of Norepinephrine Versus Epinephrine on Regional Cerebral Blood Flow During Cardiopulmonary Resuscitation," *American Journal of Emergency Medicine*, vol. 7, No. 3, May, 1989, pp. 278–282.

Brown, Charles G., M.D., FACEP et al., "Comparative Effect of Graded Doses of Epinephrine on Regional Brain Blood Flow During CPR in a Swine Model," *Annals of Emergency Medicine*, Oct., 1986, pp. 1138–1144.

Robinson, Linda A., M.D. et al., "The Effect of Norepinephrine Versus Epinephrine on Myocardial Hemodynamics During CPR," *Annals of Emergency Medicine*, Apr., 1989, pp. 336–340.

Sharff, Jeffrey A., M.D., "Effect of Time on Regional Organ Perfusion During Two Methods of Cardiopulmonary Resuscitation," *Annals of Emergency Medicine* (Part 1), Sep., 1984, pp. 649–656.

Schleien, Charles L., M.D., "Effect of Epinephrine on Cerebral and Myocardial Perfusion in an Infant Animal Preparation of Cardiopulmonary Resuscitation," *Circulation*, vol. 73, No. 4, Apr., 1986, pp. 809–817.

Kuboyama, Kazutoshi, M.D. et al., "Delay in Cooling Negates the Beneficial Effect of Mild Resuscitative Cerebral Hypothermia After Cardiac Arrest in Dogs: A Prospective, Randomized Study," *Critical Care Medicine*, vol. 21, No. 9, Sep., 1993, pp. 1348–1358.

Leonov, Yuval, M.D. et al., "Hypertension With Hemodilution Prevents Multifocal Cerebral Hypoperfusion After Cardiac Arrest in Dogs," *Stroke*, vol. 23, No. 1., Jan., 1992, pp. 45–53.

Sterz, Fritz, M.D. et al., "Hypertension With or Without Hemodilution After Cardiac Arrest in Dogs," *Stroke*, vol. 21, No. 8, Aug., 1990, pp. 1178–1184.

Bavaria, Joseph E., M.D. et al., "Myocardial Oxygen Utilization After Reversible Global Ischemia," *J Thorac Cardiovasc Surg*, vol. 100, No. 2, Aug., 1990, pp. 210–220.

Ballantyne, Christie M., M.D. et al., "Delayed Recovery of Severely 'Stunned' Myocardium With the Support of a Left Ventricular Assist Device After Coronary Artery Bypass Graft Surgery," *JACC*, vol. 10, No. 3, Sep., 1987, pp. 710–7112.

Cutler, Bruce, "The Intraaortic Balloon and Counterpulsation," *Intensive Care Medicine*, Second Edition, 1991, pp. 130–140.

Billhardt, Roger A., M.D. et al., "Cardiogenic and Hypovolemic Shock," *Medical Clinics of North America*, vol. 70, No. 4, Jul., 1986, pp. 853–874.

Swenson, Robert D., M.D. et al., "Hemodynamics in Humans During Conventional and Experimental Methods of Cardiopulmonary Resuscitation," *Circulation*, vol. 78, No. 3, Sep., 1988, pp. 630–639.

Redberg, Rita F., M.D. et al., "Physiology of Blood Flow During Cardiopulmonary Resuscitation/A Transesophageal Echocardiographic Study," *Circulation*, vol. 88, No. 2, Aug., 1993, pp. 534–542.

Otto, Charles W., "Current Concepts in Cardiopulmonary Resuscitation," *Seminars in Anesthesia*, vol. IX, No. 3, Sep., 1990, pp. 169–181.

Babbs, Charles F., M.D., PhD, "New Versus Old Theories of Blood Flow During CPR," *Critical Care Medicine*, vol. 8, No. 3, Mar., 1980, pp. 191–195.

Niemann, James T., M.D., "Differences in Cerebral and Myocardial Perfusion During Closed–Chest Resuscitation," *Annals of Emergency Medicine* (Part 2), Sep., 1984, pp. 849–853.

Niemann, James T., M.D. et al., "Predictive Indices of Successful Cardiac Resuscitation After Prolonged Arrest and Experimental Cardiopulmonary Resuscitation," *Annals of Emergency Medicine*, Jun., 1985, pp. 521–528.

Paradis, Norman A., M.D. et al., "Coronary Perfusion Pressure and the Return of Spontaneous Circulation in Human Cardiopulmonary Resuscitation," *JAMA*, vol. 263, No. 8, Feb. 23, 1990, pp. 1106–1113.

Martin, Gerard B., M.D. et al., "Aortic and Right Atrial Pressures During Standard and Simultaneous Compression and Ventilation CPR in Human Beings," *Annals of Emergency Medicine*, Feb., 1986, pp. 125–130.

Niemann, James T., M.D. et al., "Coronary Perfusion Pressure During Experimental Cardiopulmonary Resuscitation," *Annals of Emergency Medicine*, Mar., 1982, pp. 127–131.

DeBehnke, Daniel J., M.D. et al., "Comparison of Standard External CPR, Open–Chest CPR, and Cardiopulmonary Bypass in a Canine Myocardial Infarct Model," *Annals of Emergency Medicine*, Jul., 1991, pp. 754–760.

Niemann, James T., "Alternatives to Standard CPR," *Cardiopulmonary Resuscitation*, 1989, pp. 103–116.

Martin, Gerard B., M.D. et al., "Cardiopulmonary Bypass vs CPR as Treatment for Prolonged Canine Cardiopulmonary Arrest," *Annals of Emergency Medicine*, Jun., 1987, pp. 628–636.

Emerman, Charles L., M.D. et al., "Hemodynamic Effects of the Intra–aortic Balloon Pump During Experimental Cardiac Arrest," *American Journal of Emergency Medicine*, vol. 7, No. 4., Jul., 1989, pp. 378–383.

Bircher, Nicholas, AB et al., "A Comparison of Standard, 'MAST'–Augmented, and Open–Chest CPR in Dogs," *Critical Care Medicine*, vol. 8, No. 3., Mar., 1980, pp. 147–152.

Cohen, Todd J., M.D. et al., "A comparison of Active Compression–Decompression Cardiopulmonary Resuscitation With Standard Cardiopulmonary Resuscitation for Cardiac Arrests Occuring in the Hospital," *The New England Journal of Medicine*, vol. 329, No. 26, Dec., 23, 1993, pp. 1918–1921.

Safar, Peter, M.D. et al., "Emergency Cardiopulmonary Bypass for Resuscitation From Prolonged Cardiac Arrest," *American Journal of Emergency Medicine*, vol. 8, No. 1., Jan., 1990, pp. 55–67.

Griffith, Robert F. et al., "A Comparison of Three Non–Invasive Measurements for Coronary Perfusion Pressure and Prediction of Return of Spontaneous Circulation During Cardiopulmonary Resuscitation," *Critical Care Medicine*, Apr., 1993.

Buckman, Jr., Robert et al., "Minimally–Invasive Direct Cardiac Massage: Systemic Blood Flow," *Critical Care Medicine*, Apr., 1993.

Halperin, Henry R., M.D. et al., "Vest Inflation Without Simultaneous Ventilation During Cardiac Arrest in Dogs: Improved Survival From Prolonged Cardiopulmonary Resuscitation," *Circulation*, vol. 74, No. 6, Dec., 1986, pp. 1407–1415.

"A Preliminary Study of Cardiopulmonary Resuscitation by Circumferential Compression of the Chest With Use of a Pneumatic Vest," *The New England Journal of Medicine*, vol. 329, No. 11, Sep. 9, 1993, pp. 762–768.

Halperin, Henry R., M.D. et al., "Cardiopulmonary and Critical Care: New Cardiopulmonary Resuscitation Techniques," *Abstracts From the 65th Scientific Sessions, Circulation*, Supplement I, vol. 86, No. 4, Oct., 1992, pp. I-233.–I-235.

Cohen, Todd J., M.D. et al., "Active Compression–Decompression/A New Method of Cardiopulmonary Resuscitation," *JAMA*, vol. 267, No. 21, Jun. 3, 1992, pp. 2916–2923.

Alexander, Raymond H., M.D., FACS et al., "Chapter 3: Shock," *Advanced Trauma Life Support Program for Physicians*, Fifth Edition, 1993.

Moore, John B. et al., "Chapter 12: Emergency Department Thoracotomy," *Trauma*, Second Edition, 1988, pp. 181–193.

Kowalenko, Terry, M.D. et al., "Improved Outcome With Hypotensive Resuscitation of Uncontrolled Hemorrhagic Shock in a Swine Model," *The Journal of Trauma*, vol. 33, No. 3, Sep., 1992, pp. 349–353.

Stern, Susan A., M.D. et al., "Effect of Blood Pressure on Hemorrhage Volume and Survival in a Near–Fatal Hemorrhage Model Incorporating a Vascular Injury," *Annals of Emergency Medicine*, Feb., 1993, pp. 155–163.

Low, Ronald B., M.D. et al., "Preliminary Report on the Use of the Percluder® Occluding Aortic Balloon in Human Beings," *Annals of Emergency Medicine*, Dec., 1986, pp. 1466–1469.

Gupta, Bhupendra K., M.D. et al., "The Role of Intra–aortic Balloon Occlusion in Penetrating Abdominal Trauma," *The Journal of Trauma*, vol. 29, No. 8, Jun., 1989, pp. 861–865.

Landreneau, Rodney J., M.D. et al., "Splanchnic Blood Flow Response to Intraaortic Balloon Pump Assist of Hemorrhagic Shock[1]," *Journal of Surgical Research*, vol. 51, No. 4, Oct., 1991, pp. 281–287.

Tisherman, Samuel A., M.D. et al., "Therapeutic Deep Hypothermic Circulatory Arrest in Dogs: A Resuscitation Modality for Hemorrhagic Shock With 'Irreparable' Injury," *The Journal of Trauma*, vol. 30, No. 7, Jul., 1990, pp. 836–847.

Mabey, Brent Edward, "Chapter 70: Abdominal Aortic Aneurysm," *Emergency Medicine/Concepts and Clinical Practice*, Third Edition, vol. II, pp. 1372–1383.

White, Robert J., M.D., PhD et al., "The Diagnosis and Initial Management of Head Injury," *The New England Journal of Medicine*, vol. 327, No. 21, Nov. 19, 1992, pp. 1507–1511.

Gentleman, Douglas et al., "Guidelines for Resuscitation and Transfer of Patients With Serious Head Injury," *BMJ*, vol. 307, Aug. 28, 1993, pp. 547–552.

Hariri, Robert J., M.D., PhD et al., "Traumatic Brain Injury, Hemorrhagic Shock, and Fluid Resuscitation: Effects on Intracranial Pressure and Brain Compliance," *J. Neurosurg*, vol. 79, Sep., 1993, pp. 421–427.

Fulton, Robert L., M.D. et al., "Brain Injury Causes Loss of Cardiovascular Response to Hemorrhagic Shock," *Journal of Investigative Surgery*, vol. 6, pp. 117–131.

Rosner, Michael J., M.D. et al., "Cerebral Perfusion Pressure Management in Head Injury," *The Journal of Trauma*, vol. 30, No. 8, Aug., 1990, pp. 933–941.

Marion, Donald W., M.D. et al., "The Use of Moderate Therapeutic Hypothermia for Patients With Severe Head Injuries: A Preliminary Report," *J. Neurosurg.*, vol. 79, Sep., 1993, pp. 354–362.

Marion, Donald W., M.D. et al., "Acute Regional Cerebral Blood Flow Changes Caused by Severe Head Injuries," *J. Neurosurg.*, vol. 74, Mar., 1991, pp. 407–414.

Feldman, James A., M.D., F.A.C.E.P. et al., "Resuscitation Fluid for a Patient With Head Injury and Hypovolemic Shock," *The Journal of Emergency Medicine*, vol. 9, Feb. 23, 1991, pp. 465–468.

Shackford, Steven R., M.D., F.A.C.S. et al., "The Effects of Aortic Crossclamping and Resuscitation on Intracranial Pressure, Cerebral Blood Flow, and Cerebral Water Content in a Model of Focal Brain Injury and Hemorrhagic Shock," *The Journal of Trauma*, vol. 30, No. 7, Jul., 1990, pp. 768–775.

Yarbrough, Barry E. et al., "Heat–Related Illnesses," *Management of Wilderness and Environmental Emergencies*, Second Edition, 1989, pp. 119–143.

Danzyl, Daniel F. et al., "Accidental Hypothermia," *Management of Wilderness and Environmental Emergencies*, Second Edition, 1989, pp. 35–76.

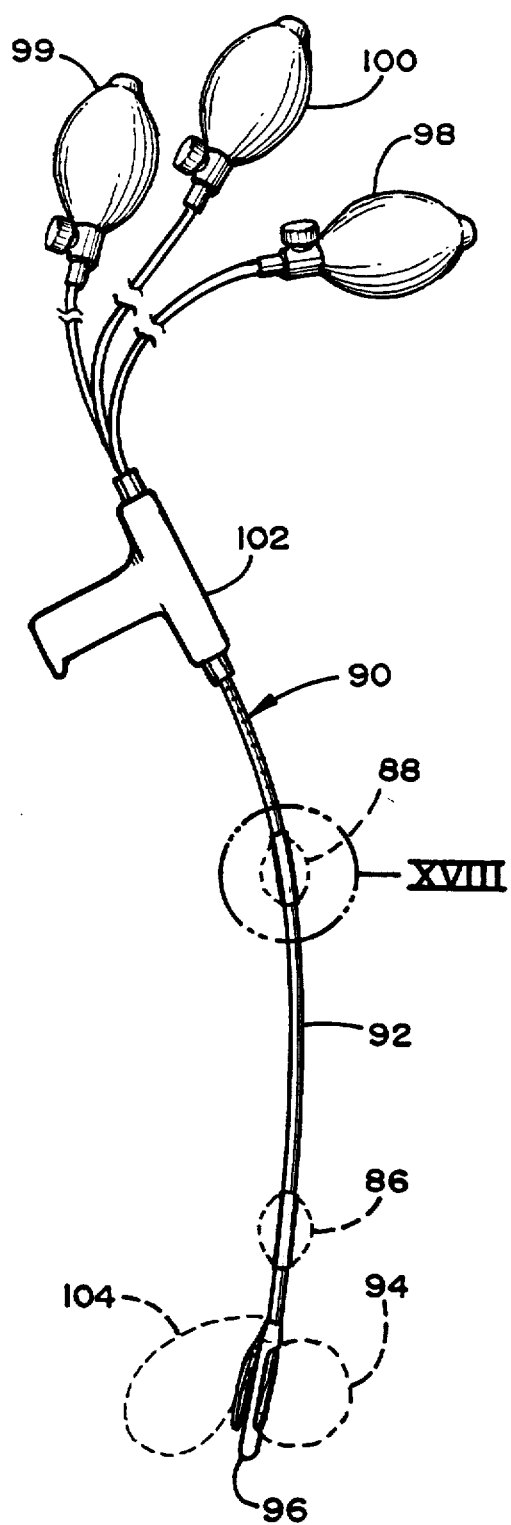
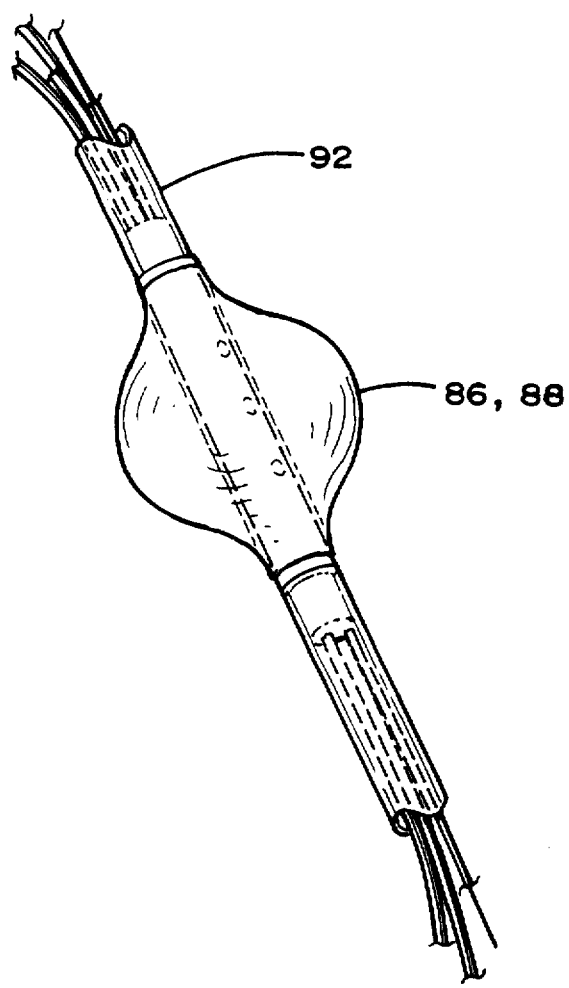
Fig 17
Fig 18

US 6,296,654 B1

NON-INVASIVE AORTIC IMPINGEMENT

This application is a 371 of PCT/US98/13109 filed Jun. 24, 1998 which claims benefit of Prov. No. 60/050,133 filed Jun. 27, 1997.

BACKGROUND OF THE INVENTION

This invention relates generally to medical intervention and, more particularly, to the treating of cardiac arrest patients, patients in various forms of shock and patients with head injury. More particularly, this invention relates to a method and apparatus for a non-invasive alteration of arterial blood pressures, myocardial and cerebral perfusion pressures, blood flow and cardiac output.

Approximately one million people per year have cardiac arrests in the United States. Less than 10% of these people are discharged from the hospital alive without neurological damage. This percentage of people discharged would be increased if the treatment available after the onset of cardiac arrest was improved. Areas in which this treatment could be improved include: (1) artificial circulation during cardiopulmonary resuscitation (CPR); (2) induction and maintenance of brief periods of cerebral hypertension after return of spontaneous circulation; and (3) continued circulatory support for the brain and heart after return of spontaneous circulation from cardiac arrest.

The blood of a cardiac arrest patient is artificially circulated during CPR by cyclically compressing the chest. One major theory describing how artificial circulation is generated during CPR states that compression of the chest causes global increases in intrathoracic pressure. This increase in intrathoracic pressure in the thoracic compartment is evenly distributed throughout the lungs and the four chambers of the heart, as well as the great vessels in the chest. The increase in thoracic pressure is greater than in the compartments above and below the chest. These compartments mainly include the neck and head above the chest and the abdominal compartment below the diaphragm and the chest. When thoracic pressure is increased above the pressure in these compartments, blood within the thoracic cavity moves to the head and abdomen with greater blood flow going toward the head. When the chest is released, the pressure within the thoracic cavity drops and becomes less than the pressure within the head and abdomen, therefore allowing blood to return to the thoracic cavity from the head and abdominal compartments. This theory of CPR-produced blood flow is termed the "thoracic pump mechanism," whereby the entire thorax itself acts as a pump with the heart itself acting as a passive conduit for blood flow. This theory is different from the cardiac pump mechanism, which states that compression of the chest produces blood flow by compressing the heart between the sternum and anterior structures of the vertebral column. In most patients, blood flow produced during chest compressions is likely a combination of the two theories. In each individual patient, blood flow during CPR depends on various factors, such as body habitus, with thinner individuals relying more on the cardiac pump mechanism of blood flow, and in larger individuals with increased anterior-posterior chest dimension relying on the thoracic pump mechanism. Both mechanisms of blood flow have been shown to be present in animal and human studies. Regardless of which mechanism is invoked, currently performed standard chest compressions as recommended by the American Heart Association produces 30% or less of the normal cardiac output. This results in extremely poor regional cerebral and myocardial blood flow during CPR. The level of blood flow generated during CPR is usually insufficient to re-start the heart and prevent neurologic damage. The purpose of CPR is to attempt to sustain the viability of the heart and brain until more definitive measures, such as electrical countershock and pharmacotherapy, are administered to the patient.

A main determinant for successful resuscitation from cardiac arrest is the coronary perfusion pressure produced during CPR. Coronary perfusion pressure (CPP) is defined as the aortic diastolic pressure minus the right atrial diastolic pressure. CPP represents the driving force across the myocardial tissue bed. Animal studies are plentiful which demonstrate that CPP is directly related to myocardial blood flow. It appears in humans that a CPP of at least 15 mm Hg is required for successful resuscitation. CPP of this magnitude is difficult to achieve with chest compressions alone. Patients, who utilize the thoracic pump mechanism for CPR, are even more unlikely to be able to produce this level of CPP during CPR alone. The major means for producing coronary perfusion pressures high enough for successful resuscitation have been to perform more forceful chest compressions and by administering various adrenergic agonists, such as epinephrine. Unfortunately, it has been shown that CPPs are difficult to augment with chest compressions alone and that in some situations very high doses of adrenergic agonists are required to produce higher CPPs. The difficulty in trying to produce higher CPPs with CPR alone lies in the fact that right atrial diastolic pressures are sometimes increased to the same or greater magnitude as aortic diastolic pressures. Using various adrenergic agonists, aortic diastolic pressure is usually augmented to a higher degree than right atrial diastolic pressure. However, the use of adrenergic agonists to achieve this have several drawbacks. These include increasing myocardial oxygen demands to a greater degree than can be met with blood flow produced during CPR. In addition, there are lingering effects of adrenergic agonists which may be detrimental after successful return of spontaneous circulation. These include periods of prolonged hypertension and tachycardia, which may further damage the heart and possibly cause re-arrest.

Cerebral perfusion pressure is a main determinant of cerebral blood flow. During cardiac arrest and CPR, autoregulation of blood flow in the brain may be lost. Cerebral perfusion pressure is defined as the mean arterial pressure minus the intracranial pressure. The main determinant of mean arterial pressure during CPR is aortic diastolic pressure. One of the main determinants of intracranial pressure during CPR is the mean venous pressure in the central circulation and the neck. Forward flow to the head is produced during CPR because of functional valves at the neck veins entering the thorax. These valves close during chest compressions, which prevent venous pressure transmission and flow of blood back into the neck and cranium. When these valves are not functioning, pressure is transmitted during the chest compression to the neck veins and into the cranium. This in effect decreases forward cerebral blood flow. Methods that increase cerebral blood flow during conventional CPR are mainly the use of adrenergic agonists. These agents selectively increase arterial pressure over venous pressure. Thus, mean arterial pressure becomes greater than intracranial and cerebral venous pressure thus producing net forward flow. However, use of adrenergic agonists have several drawbacks. In conventional doses, increases in cerebral blood flow are extremely variable with many individuals having no response at all. The use of higher doses of adrenergic agonists may be problematic as previously discussed under myocardial blood flow.

In summary, the major deficiencies in CPR-produced blood flow to the critical organs of the heart and brain are primarily due to the inability of conventionally performed CPR to cause highly selective increases in aortic diastolic pressure without causing increases of similar magnitude in central venous pressures. The ability to maximize the former while minimizing the latter would be extremely advantageous especially if the effects could be immediately reversed.

Several techniques have been developed to take advantage of the various CPR-produced mechanisms of blood flow. Two techniques that take advantage of the thoracic pump mechanism include simultaneous ventilation compression CPR (SVC-CPR) and vest-CPR. SVC-CPR is a technique that involves inflating the lungs simultaneously during the chest compression phase of CPR. This causes larger increases in intrathoracic pressure than external chest compression alone without ventilation or without external chest compression. This has been shown in animal studies to result in higher cerebral blood flows than in conventionally performed CPR. However, one major drawback is that coronary perfusion pressures are not uniformly increased and, in some instances, can be detrimentally decreased. When SVC-CPR was tested in a clinical trial, no increases in survival were noted over standard CPR.

Vest-CPR is a technique which utilizes a bladder containing vest analogous to a large blood pressure cuff and is driven by a pneumatic system. The vest is placed around the thorax of the patient. The pneumatic system forces compressed air into and out of the vest. When the vest is inflated, a relatively uniform decrease in circumferential dimensions of the thorax is produced which creates an increase in intrathoracic pressure. Clinically, the vest apparatus is cyclically inflated 60 times per minute with 100 mm Hg-250 mm Hg pressure which is maintained for 30%–50% of each cycle with the other portion of the cycle deflating the vest to 10 mm Hg. Positive pressure ventilation is performed independent of the apparatus after every fifth cycle. When studied clinically in humans, and compared with manually performed standard external CPR, the vest apparatus produced significantly higher coronary perfusion pressures and significantly higher mean aortic, peak aortic, and mean diastolic pressures. However, these changes are not uniformly seen in all patients. Of note, when the vest has been studied in the laboratory and clinical settings, larger doses of epinephrine have been used to achieve these higher coronary perfusion pressures since the thoracic pump model would predict aortic diastolic and right atrial diastolic pressures to be equivalent during the relaxation phase (when coronary perfusion occurs).

Another new technique, which takes some advantage of both the thoracic and cardiac pump mechanism of blood flow, is called "active compression/decompression CPR (ACDC-CPR)." This technique utilizes a plunger-type device, which is placed on the patient's sternum during cardiac arrest. The person performing chest compressions presses on the device which causes downward excursion of the anterior chest wall. The person then pulls up on the device. Since the device is attached to the sternum by suction, this causes the anterior chest to be actively recoiled instead of undergoing the usually passive recoil of standard external CPR. This active recoil is capable, in many individuals, of causing a decrease in intrathoracic pressure, which is transmitted to the right atrium thus lowering right atrial pressure during artificial diastole and, in turn, increasing coronary perfusion pressure. This negative right atrial pressure also has the effect of increasing venous return to the thoracic cavity, which may enhance cardiac output. Factors, such as body habitus and chest wall compliance, which impact on the efficacy of ACDC-CPR have not been studied, but are likely to have an effect. Persons with larger body habitus probably would receive less benefit from the technique.

Two other techniques, which are being investigated to resuscitate victims of cardiac arrest, and which do not rely on a mechanism of CPR-produced blood flow, include selective aortic arch perfusion and cardiopulmonary bypass. Both of these techniques require access to the central arterial vasculature. Selective aortic perfusion is experimental and involves percutaneously placing a balloon catheter in the aortic arch through a vessel, such as the femoral artery. The balloon catheter is placed in the aortic arch and the inflated balloon positioned just distal to the take-off of the carotid arteries. Perfusion takes place under pressure with oxygenated fluids or blood for various lengths of time. In this manner, the brain and heart are selectively perfused with little or no perfusion taking place distal to the occluded portion of the aorta. Over time, the central venous pressures will rise. This technique has not been tested clinically, but is expected to take a high level of expertise and cannot be readily performed in a setting outside of the hospital where many cardiac arrests occur.

Cardiopulmonary bypass during CPR is performed by obtaining central arterial and venous access usually percutaneously through the femoral artery and vein. This technique is capable of totally supporting the circulation by producing near normal cardiac outputs and blood flows to the heart and brain. Although shown to be effective, there are many technical difficulties which make its widespread use unfeasible. Large cannulas must be placed in the femoral artery and vein, which is difficult in the collapsed circulation. The bypass circuit is complicated and, if not properly primed, may produce air emboli. In addition, the patient requires systemic anticoagulation in most instances. The use of such a technique during CPR can be performed only at specially equipped centers with specially trained personnel.

Open-chest CPR is an old technique that was commonly performed before the advent of modern-day CPR. This technique involves opening the patient's chest by performing a thoracotomy. The descending aorta is usually cross-clamped. The heart itself is then manually massaged (compressed) with the hands. Although this technique is effective in producing heart and brain blood flows superior to standard CPR, it does not lend itself to widespread performance especially in the out-of-hospital setting. Reasons for this include the level of expertise required and the hazard of blood-borne pathogens. Other special equipment, such as the Anstadt cup, can be directly placed on the heart to mechanically compress the heart but, of course, have the same disadvantage of requiring a thoracotomy.

Two post-resuscitative interventions found to improve neurologic outcome in animal models of cardiac arrest is a brief period of immediate post-resuscitation hypertension and rapid induction and maintenance of cerebral hypothermia. The mechanisms for improved neurologic outcome with post-resuscitation hypertension is unclear. It is thought that this brief period of hypertension clears cerebral vessels of microthrombi, which may clog the cerebral circulation following cardiac arrest. It is also thought that this brief period of hypertension may help to prevent some of the post-resuscitation cerebral low flow and "no flow phenomenon," which contributes to neurologic injury. Post-resuscitation hypertension may decrease the overall amount of cerebral damage caused by cardiac arrest. One difficulty in providing for post-resuscitation hypertension is that the common means of producing this, through the use of adrenergic agonists, also produces considerable metabolic demands on the cardiovascular system.

Cardiogenic shock has many causes, including myocardial infarction, various forms of myocarditis, and other causes of myocardial injury. When severe, this condition becomes self-perpetuating secondary to the inability of the host to provide for adequate myocardial blood flow. This may result in further myocardial dysfunction leading to inadequate cerebral and myocardial blood flow and eventually to cardiac arrest. Cardiogenic shock may also be first noted after resuscitation from cardiac arrest depending on the length of the cardiac arrest. Cardiogenic shock may sometimes be difficult to distinguish from other forms of shock. Survival might be enhanced if myocardial and cerebral perfusion could be maintained until other definitive diagnostic and therapeutic measures could take place.

Immediate survival from cardiogenic shock will depend on maintenance of myocardial and cerebral blood flow. Various forms of treatment are available for cardiogenic shock, including various forms of pharmacotherapy and intra-aortic balloon pumping. Pharmacotherapy, while effective, requires invasive hemodynamic monitoring, such as pulmonary artery catheter placement for optimal titration. This may be difficult to institute in a timely manner when severe cardiogenic shock is first encountered especially in the pre-hospital setting. Intra-aortic balloon pumping in which a balloon catheter is placed into the thoracic aorta is effective but somewhat complicated to perform. Special equipment is needed for its placement and can only be performed at facilities which are capable of placing and maintaining such equipment and patients. Intra-aortic balloon pumping increases cardiac output by decreasing cardiac afterload. A balloon inflates during the diastolic portion of a cardiac cycle. This reduces cardiac afterload, thus lessening the workload on the heart. This balloon inflation during diastole also forces blood cephalad, thus perfusing the myocardial and cerebral tissues more effectively.

Other forms of shock, such as septic and neurogenic shock, cause hypoperfusion of critical organs due to a relative hypovolemia. Vascular tone is lost and requires a combination of volume replacement and vasopressors to maintain critical perfusion to vital organs. Immediate effective therapy aimed at maintaining cerebral and myocardial perfusion is difficult to institute because the various forms of shock are at times difficult to differentiate and therapy may differ between types of shock, although the immediate goal is to preserve myocardial and cerebral perfusion.

The major underlying immediate cause of death from any shock state is inadequate myocardial and cerebral perfusion. Survival with intact neurologic function is likely to be enhanced if myocardial and cerebral blood flow can be maintained until the underlying cause of the shock state can be optimally diagnosed and treated.

Head injury can be devastating. Much of the neurologic damage that takes place occurs after the initial insult. Blood flow to injured brain tissue is many times reduced below critical levels required to maintain survival when intracranial pressure is increased. Cerebral blood flow may be extremely difficult to maintain after the initial injury especially when multiple organ systems are involved in the trauma. Mean arterial blood pressure can also be difficult to maintain because of the ongoing blood loss into the thoracic and abdominal cavities or from extremity injuries. Intracranial pressure increases because of brain edema from the cerebral injury, or from expanding pools of blood from torn vessels in the brain or skull itself. Currently, the main mechanisms for reducing intracranial pressure involve the administration of diuretics, such as furosemide and mannitol, administration of steroids which reduce cerebral edema over time, removal of cerebral spinal fluid, elevation of the head which promotes venous drainage, administration of barbiturates which reduce the metabolic demand of brain tissue, hyperventilation producing hypocapnia and reduced cerebral blood flow which decreases intracranial pressure, and, as a last resort, removal of less necessary parts of the brain itself. Many of these therapies cannot be performed during the initial care of the multiple injured trauma patient who has both neurologic injury and multiple organ system injury, or have significant side effects. Administration of diuretics produce further volume depletion and may further reduce mean arterial pressure. Steroids require several hours to begin taking effect. Removal of cerebral spinal fluid and damaged brain tissue itself may take several hours to perform. Administration of barbiturates may also reduce the mean arterial pressure. Hyperventilation, although effective in reducing intracranial pressure, does so by decreasing cerebral blood flow which may be injurious to damaged tissue. All of these therapies become more complicated in the presence of other extra-cerebral organ injury. Occasionally, pharmacotherapy to raise mean arterial blood pressure is used to help maintain cerebral perfusion pressure in the face of rising intracranial pressure. This is difficult and sometimes dangerous to institute early because vasopressors many times increase the metabolic demands of other injured tissues.

Hemorrhagic shock is a leading cause of death from trauma. Many times there are delays in reaching hospitals which are qualified to take care of the complex injuries of such individuals. Many patients who die of trauma, die from multi-system involvement. Multi-system involvement may include head injury along with injuries to organs of the thoracic and abdominal cavity. Uncontrolled hemorrhage leading to hypovolemic shock is a leading cause of death from trauma especially from blunt and penetrating trauma of the abdomen. When head trauma occurs concomitantly with thoracic and abdominal hemorrhage, the brain becomes hypoperfused and, thus, becomes at greater risk for secondary injury. Currently, in the pre-hospital and emergency department setting, there are limited means to control exsanguinating hemorrhage below the diaphragm while maintaining myocardial and cerebral blood flow. Definitive control of hemorrhage is performed at surgery but this may be delayed and may not occur within the golden hour (time from injury to definitive treatment/repair) where the best opportunity lies in salvaging the patient. Survival with improved neurologic outcome might be enhanced if means were available to slow or stop ongoing hemorrhage (especially below the diaphragm) while maintaining adequate perfusion to the heart and brain until definitive treatment of the hemorrhage is available. This would be especially true of trauma victims whose transport to appropriate medical facilities would be prolonged.

The use of the pneumatic anti-shock garment (PASG) has met with varying degrees of success depending on the location of injury. This garment is placed on the legs and abdomen and is then inflated. Hemorrhage in the abdominal cavity, as well as the lower extremities, is controlled through tamponade while systemic blood pressure is raised partially through autotransfusion and by raising peripheral vascular resistance. Use of the PASG can sometimes be cumbersome and does not uniformly control hemorrhage or raise blood pressure. In addition, persons with concomitant penetrating thoracic injuries may hemorrhage more when the device is applied. The device may also raise intracranial pressure, which might detrimentally alter cerebral blood flow resulting in neurologic injury.

Other more drastic means to control abdominal bleeding prior to surgery have been the use of thoracotomy to cross-clamp the thoracic aorta and the use of balloon catheters placed into the aorta from the femoral arteries to a point above the celiac-aortic axis. These techniques have met with varying degrees of success and require a high degree of skill and cannot be performed in hospitals not equipped to care for trauma patients or by paramedical care personnel.

Deliberately keeping hemorrhaging trauma victims in a hypotensive state is currently being examined as a means to improve survival. This is done based on the premise that overall hemorrhage (especially abdominal hemorrhage) is reduced if mean arterial pressure is kept low by not aggressively volume-repleting the victim prior to surgery. Unfortunately, this may be dangerous for trauma victims with concomitant head injury or myocardial dysfunction.

An important cause of hemorrhagic shock not caused by trauma includes rupture of abdominal aortic aneurysms. These can occur suddenly and without warning. Control of bleeding even at surgery can be difficult. Temporary measures discussed above for hemorrhage secondary to trauma have been tried for hemorrhage secondary to aneurysm rupture. The same difficulties apply. Survival might be enhanced if hemorrhage could be controlled earlier while maintaining perfusion to the heart and brain.

SUMMARY OF THE INVENTION

The present invention provides a non-invasive method and apparatus for enhancing cerebral and myocardial perfusion in a patient, particularly cardiac arrest patients, and for hemorrhage control of a patient for management of trauma.

A non-invasive method of subdiaphragm hemorrhage control in a patient or of enhancing cerebral and myocardial perfusion in a patient particularly during cardiopulmonary resuscitation includes positioning a moveable surface through the patient's esophagus adjacent the patient's esophageal-gastric junction. The moveable surface is displaced thereby applying a force posteriorly in the direction of the patient's descending aorta sufficiently to at least partially occlude the descending aorta. This decreases or stops hemorrhage distal the point of occlusion and increases myocardial and cerebral perfusion by increasing central and intracranial arterial pressure.

According to another aspect of the invention, a non-invasive method of subdiaphragm hemorrhage control in a patient or of enhancing cerebral and myocardial perfusion in a patient includes positioning an inflatable device through the patient's esophagus in a portion of the patient's stomach juxtaposed with the patient's descending aorta. The inflatable device is inflated and a force is applied with the inflatable device posteriorly in the direction of the patient's descending aorta sufficient to at least partially occlude the descending aorta. This decreases or stops hemorrhage distal the point of occlusion and increases myocardial and cerebral perfusion by increasing central and intracranial arterial pressure.

A non-invasive apparatus according to an aspect of the invention for at least partially occluding the descending aorta of a patient includes a tubular member configured at least in part to a patient's esophagus having a selectively moveable portion positioned adjacent the patient's esophageal-gastric junction when the tubular member is positioned in a patient's esophagus. The moveable portion is moveable a sufficient distance and has a surface of sufficient area to at least partially occlude the patient's descending aorta. A displacement mechanism is provided for displacing the moveable portion in the direction of the patient's descending aorta with a force sufficient to cause at least partial occlusion of the patient's descending aorta.

According to yet an additional aspect of the invention, a non-invasive apparatus for at least partially occluding the descending aorta of a patient includes an inflatable member and a positioning device which positions the inflatable member through the patient's esophagus in a portion of the patient's stomach juxtaposed with the patient's descending aorta. An inflation mechanism is provided which selectively inflates the inflatable member. A force-producing mechanism is provided producing a force with a surface of the inflatable member posteriorly in the direction of the patient's descending aorta sufficient to cause at least partial occlusion of the patient's descending aorta.

According to yet an additional aspect of the invention, a non-invasive apparatus for at least partially occluding the descending aorta of a patient includes an inflatable member and an elongated member which positions the inflatable member through the patient's esophagus either in a portion of the patient's stomach juxtaposed with the patient's descending aorta or adjacent the patient's esophageal-gastric junction. An inflation mechanism is provided which selectively inflates the inflatable member. A displacement mechanism is provided which is operable to displace the inflatable member from the elongated member posteriorly in the direction of the patient's descending aorta thereby producing a force posteriorly in the direction of the patient's descending aorta sufficient to at least partially occlude the descending aorta.

The invention provides hemorrhage control to a trauma patient. Additionally, by inhibiting flow of blood below the diaphragm, perfusion to critical organs, particularly during cardiopulmonary resuscitation, is increased. In this manner, the present invention provides an adjunct to enhance the effectiveness of CPR.

These and other objects, advantages and features of this invention will become apparent upon review of the following specification in conjunction with the drawings.

BRIEF DESCRIPTION OF THE DRAWINGS

FIG. 17 is a perspective view of another alternative embodiment of a non-invasive apparatus for at least partially occluding the descending aorta of a patient;

FIG. 18 is an enlargement of each area designated XVIII—XVIII in FIG. 17;

DESCRIPTION OF THE PREFERRED EMBODIMENT

Figure 1:
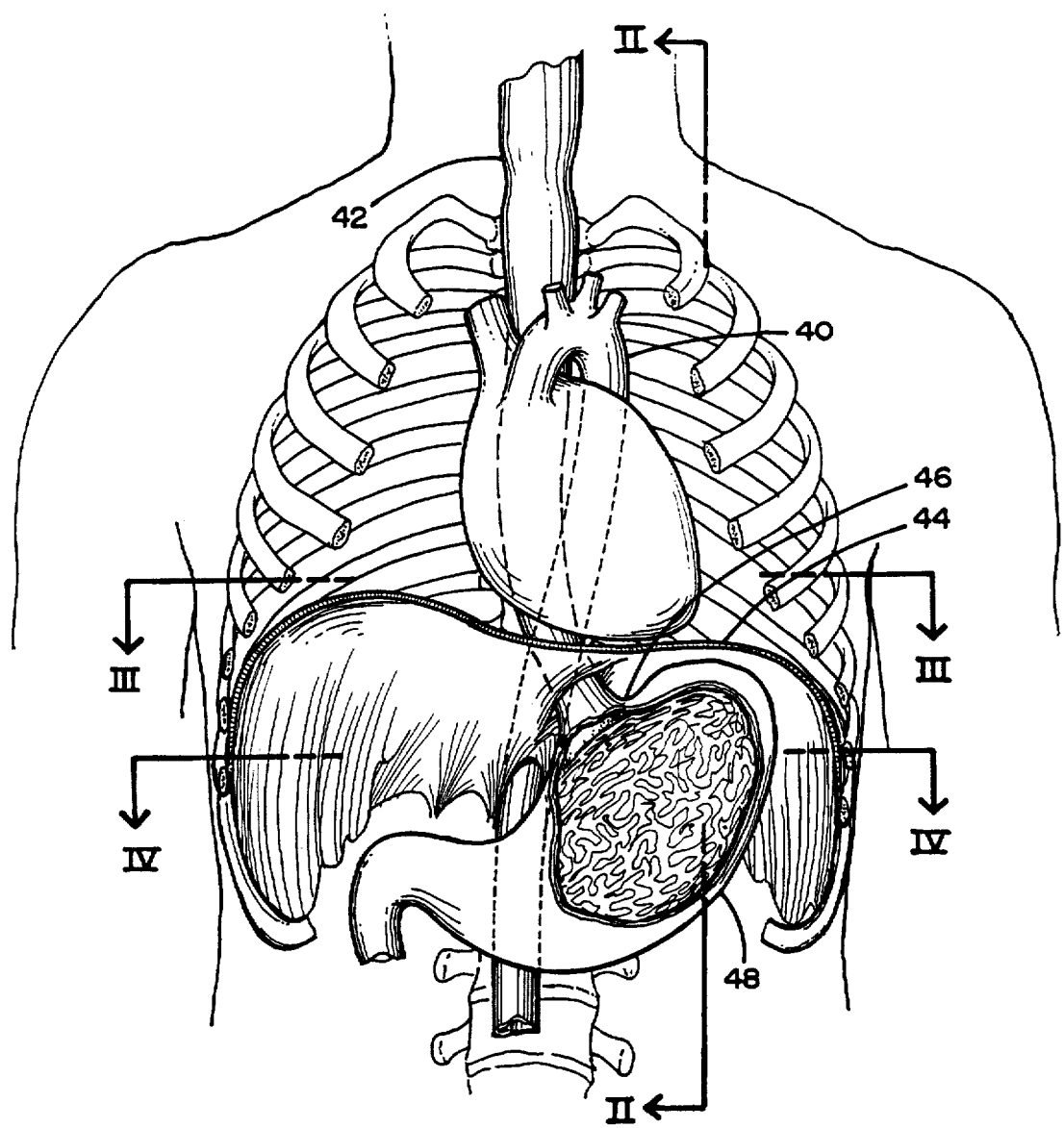
FIG. 1 is a sectional view through the frontal plane of a patient illustrating relationships between organs relevant to the invention.
Figure 2:
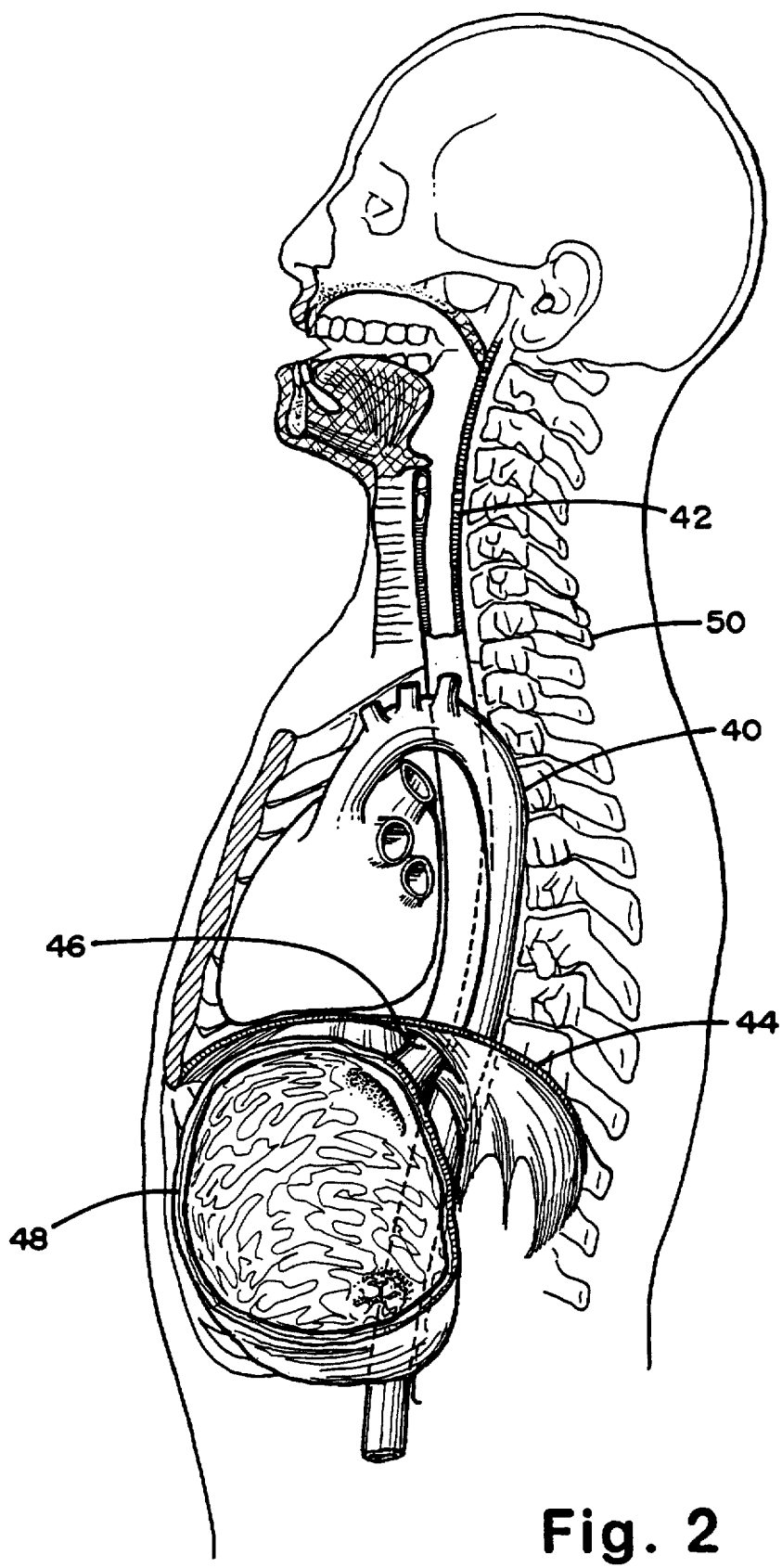
FIG. 2 is a sectional view taken along the lines II—II in FIG. 1.
Figure 3:
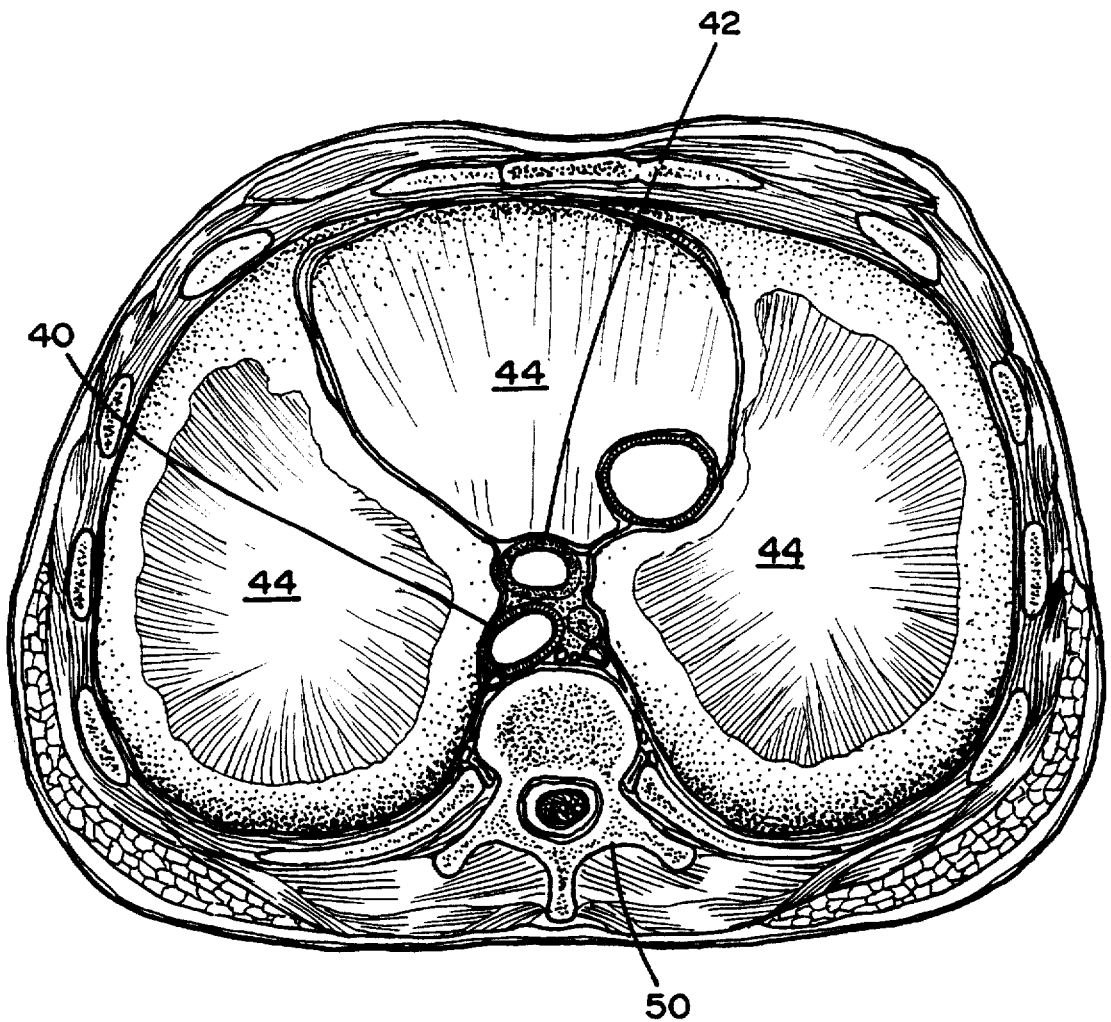
FIG. 3 is a sectional view taken along the lines III—III in FIG. 1.
Figure 4:
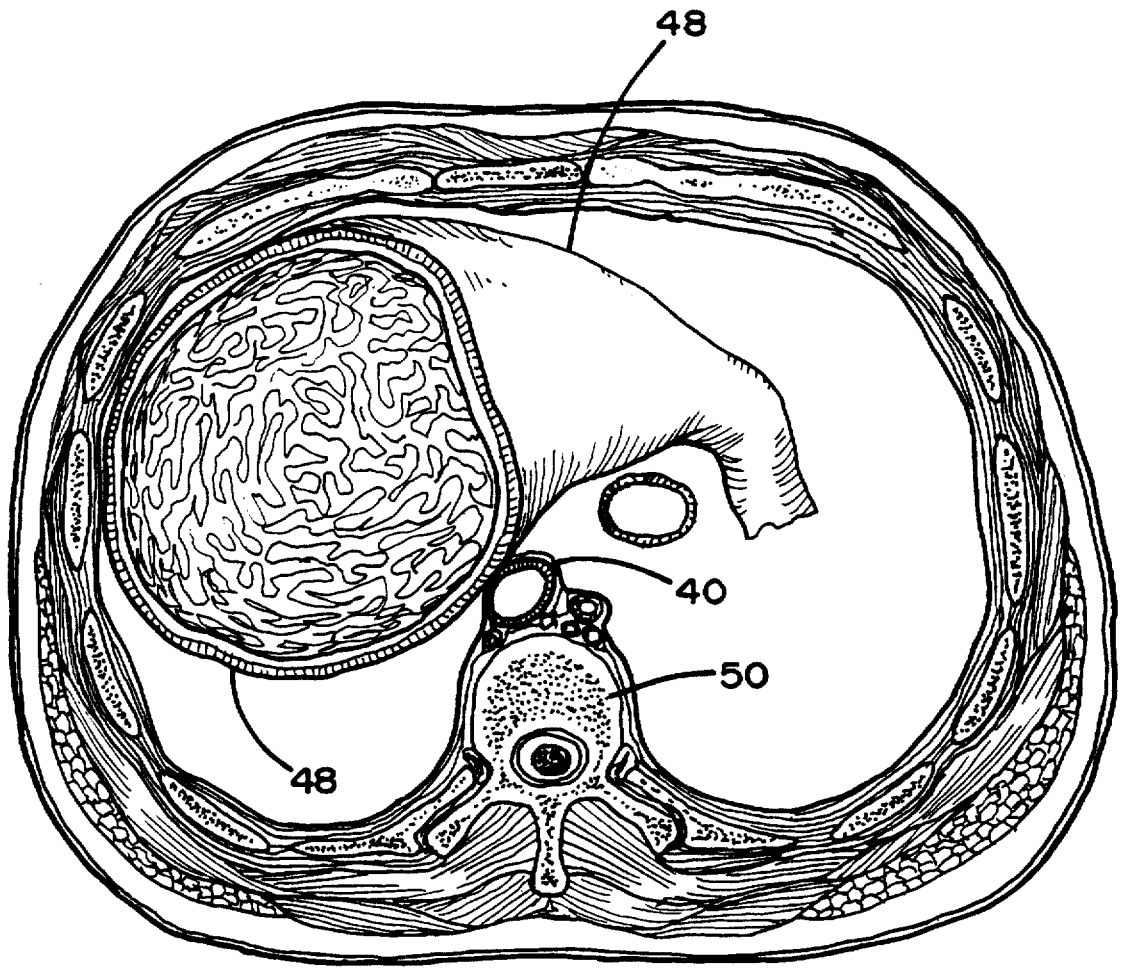
FIG. 4 is a sectional view taken along the lines IV—IV in FIG. 1.
Figure 5:
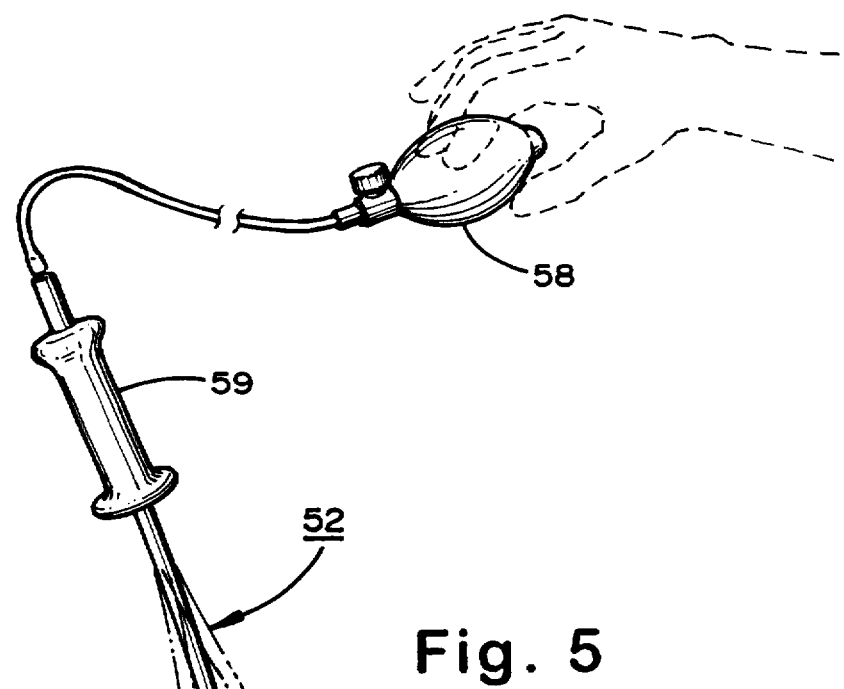
FIG. 5 is a perspective view of a non-invasive apparatus for at least partially occluding the descending aorta of a patient according to the invention.
Figure 12:
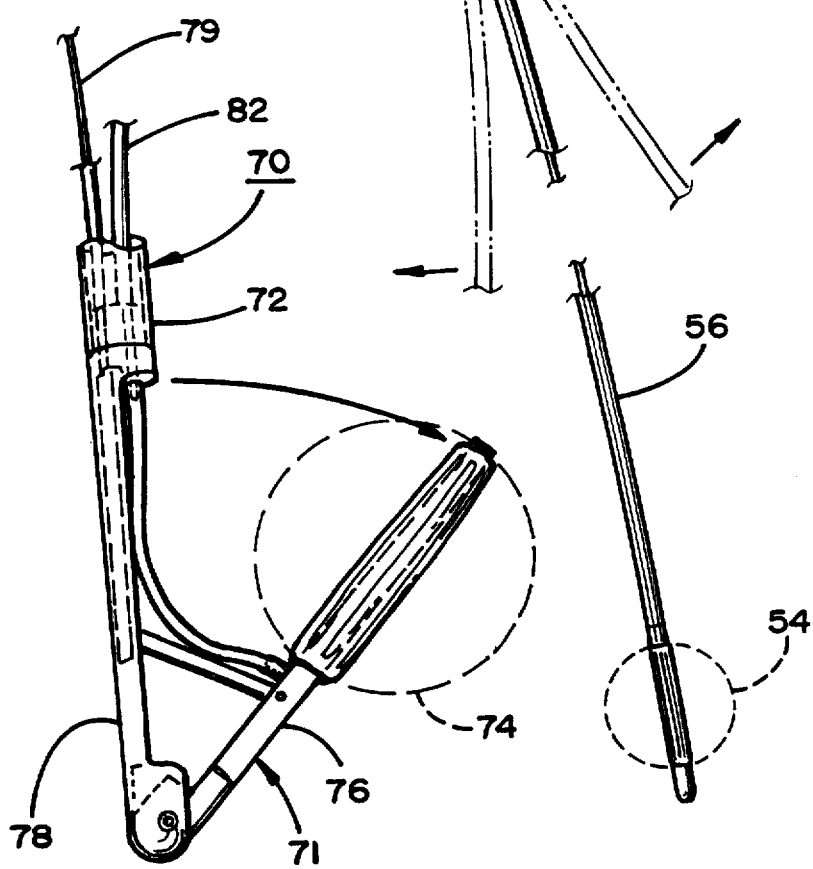
FIG. 12 is an enlarged partial perspective view of another alternative embodiment of a non-invasive apparatus for at least partially occluding the descending aorta of a patient.

Referring now specifically to the drawings, and the illustrative embodiments depicted therein, in U.S. Pat. No. 5,531,776 for a NON-INVASIVE AORTIC IMPINGEMENT AND CORE AND CEREBRAL TEMPERATURE MANIPULATION METHOD, the disclosure of which is hereby incorporated herein by reference, I disclosed a non-invasive technique for partially or completely occluding the descending aorta based upon the realization that the majority of the population has the same relationship of the esophagus to the descending aorta. The method includes positioning a device, having an elongated tubular member, in a portion of the patient's esophagus juxtaposed with the patient's descending aorta and displacing with the tubular member a wall of the portion of the esophagus posteriorly-laterally in the direction of the descending aorta. This provides at least partial occlusion of the descending aorta and thereby increases central and intracranial arterial pressure without increasing central and intracranial venous pressure. This, in turn, causes an immediate increase in myocardial and cerebral perfusion and thereby provides an adjunct to cardiopulmonary resuscitation (CPR). Additionally, the method may be used during hemorrhagic shock in order to decrease blood loss.

As can be seen by reference to FIGS. 1–4, the descending aorta 40 is juxtaposed with the esophagus 42 throughout a significant portion of the thoracic cavity. However, the esophagus and descending aorta are most closely bound where they mutually pass in close proximity through the diaphragm 44 just above the esophageal-gastric junction 46. Below the diaphragm, the descending aorta 40 passes posteriorly of the stomach 48 between the stomach and vertebral spinal column 50. The present invention is based upon a discovery that, because the descending aorta and esophagus are tightly bound in close proximity where they pass through the diaphragm, manipulation of a device positioned adjacent the esophageal-gastric junction may be used to deflect or expand the esophagus and/or stomach and thereby at least partially occlude the aorta against the vertebral column.

To carry out such non-invasive partial or complete occlusion of the aorta requires proper positioning both longitudinally and radially of a surface which is moveable laterally a sufficient distance, with a sufficient force, and having a surface of sufficient area to at least partially occlude the patient's descending aorta. This is accomplished in the various embodiments of the invention in a manner which overcomes the difficulties of proper positioning of the moveable surface notwithstanding the great variety in the anatomy of a patient, as will be described in more detail below.

A non-invasive apparatus 52 for at least partially occluding the descending aorta of a patient includes a force-producing surface, defined by an inflatable member 54, and a positioning device, in the form of an elongated member 56, for positioning inflatable member 54 through the patient's esophagus in a portion of the patient's stomach 48 which is juxtaposed with the patient's descending aorta 40. Apparatus 52 further includes an inflation mechanism 58 which selectively inflates inflatable member 54 and a force-producing mechanism, in the form of a handgrip 59 affixed to a distal end of elongated member 56, which produces a force, with the surface of inflatable member 54, posteriorly-laterally in the direction of the patient's descending aorta sufficient to cause either partial, or substantially complete, occlusion of the patient's descending aorta.

Figure 6:
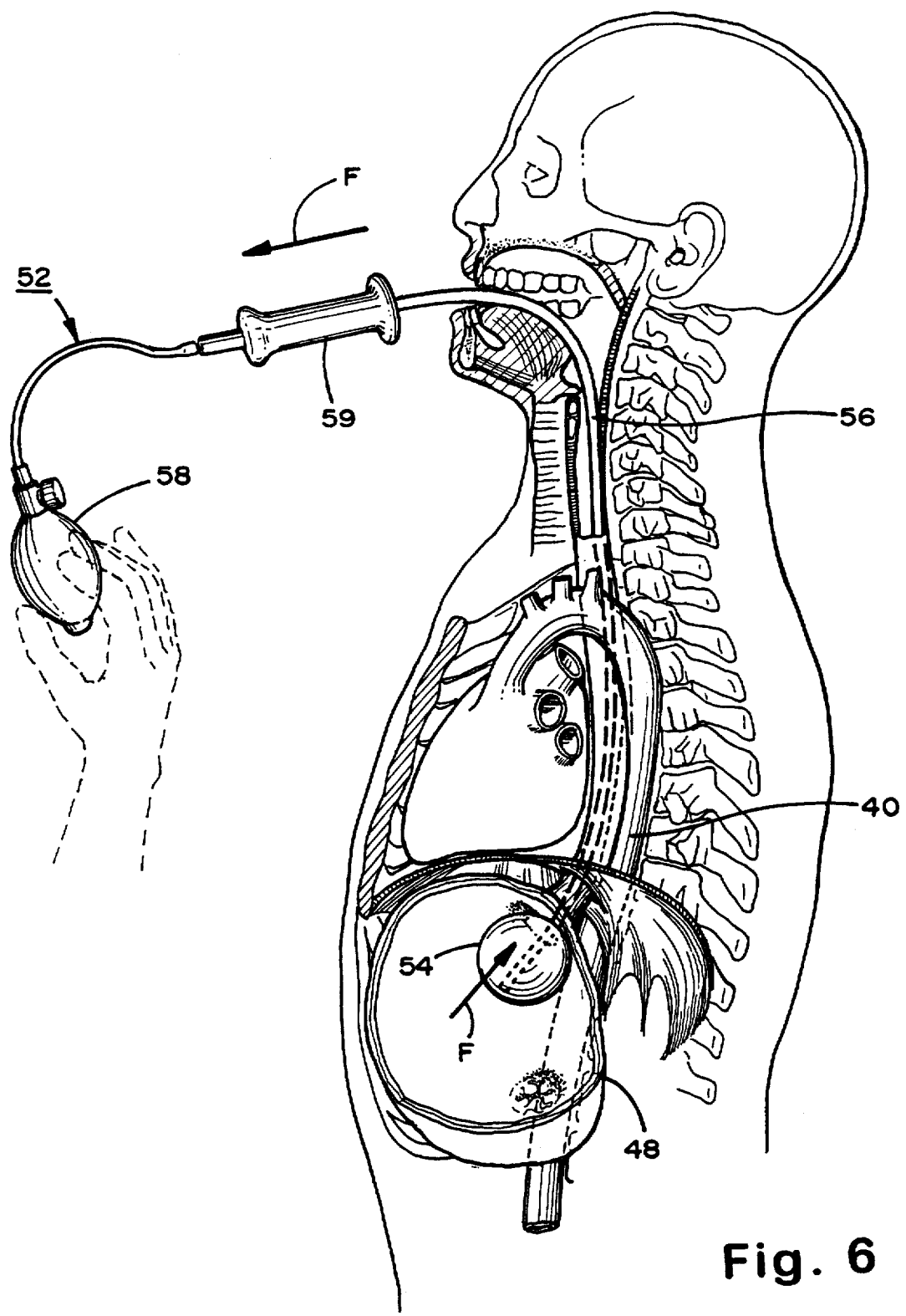
FIG. 6 is the same view as FIG. 2 illustrating the apparatus in FIG. 5 being utilized to enhance cerebral and myocardial perfusion in a patient or treat shock in a patient.
Figure 7:
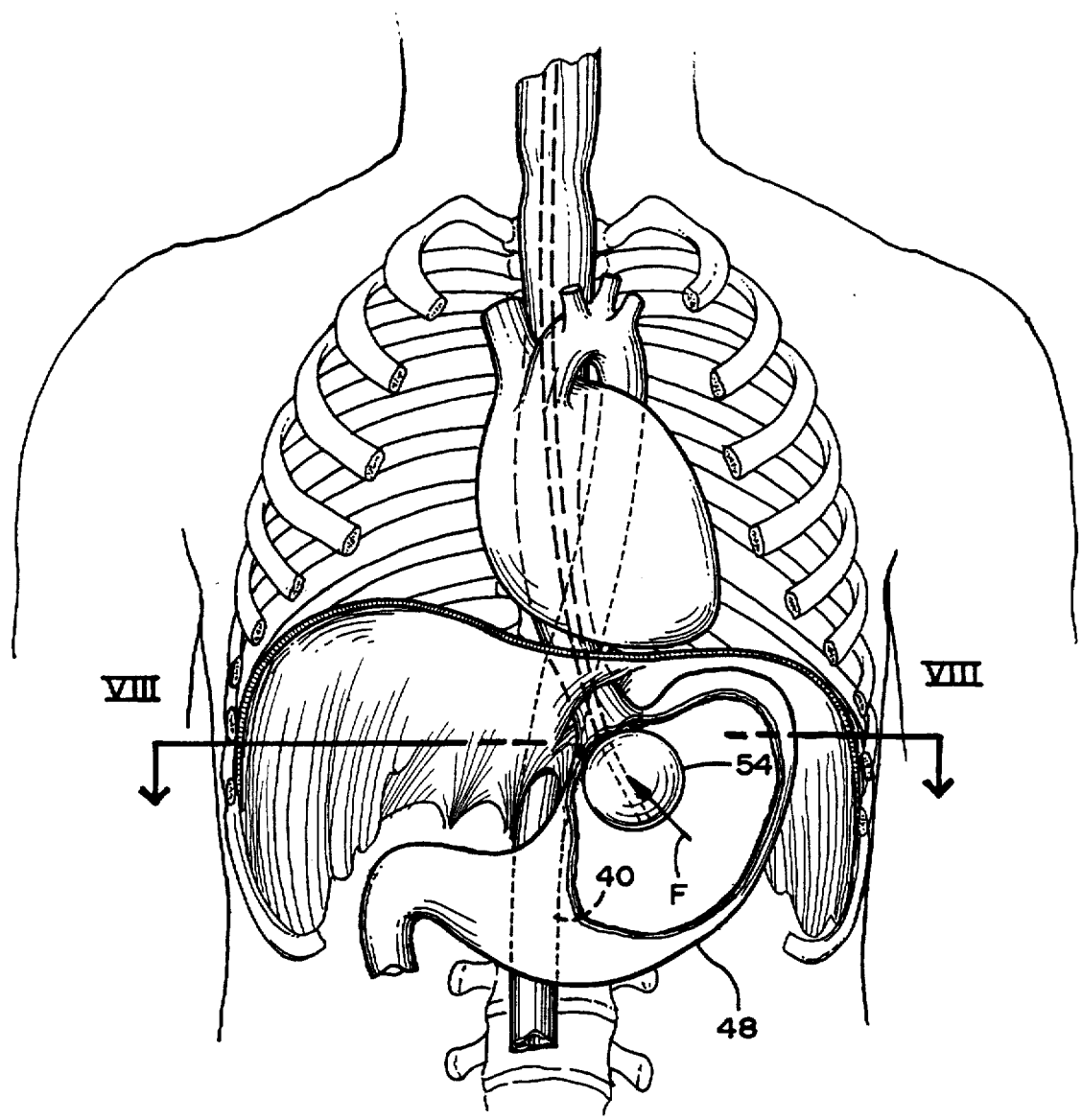
FIG. 7 is the same view as FIG. 1 of the method and apparatus illustrated in FIG. 6.
Figure 8:
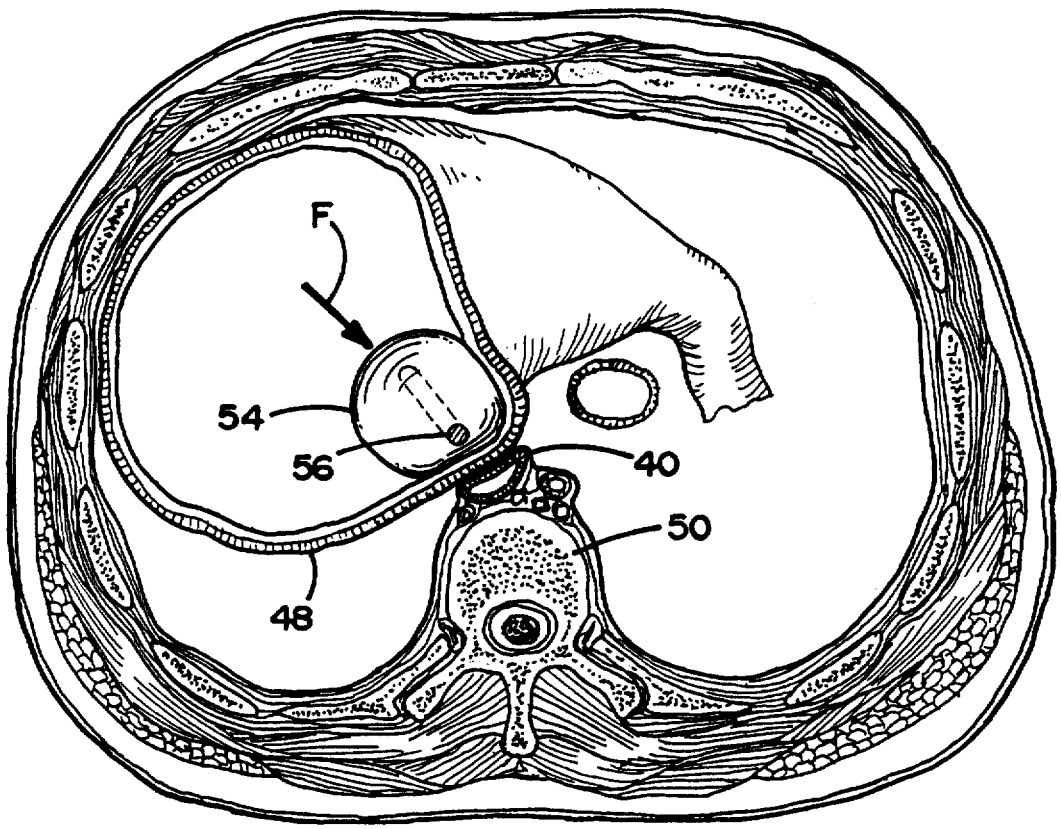
FIG. 8 is a sectional view taken along the lines VIII—VIII in FIG. 7.
Figure 9:
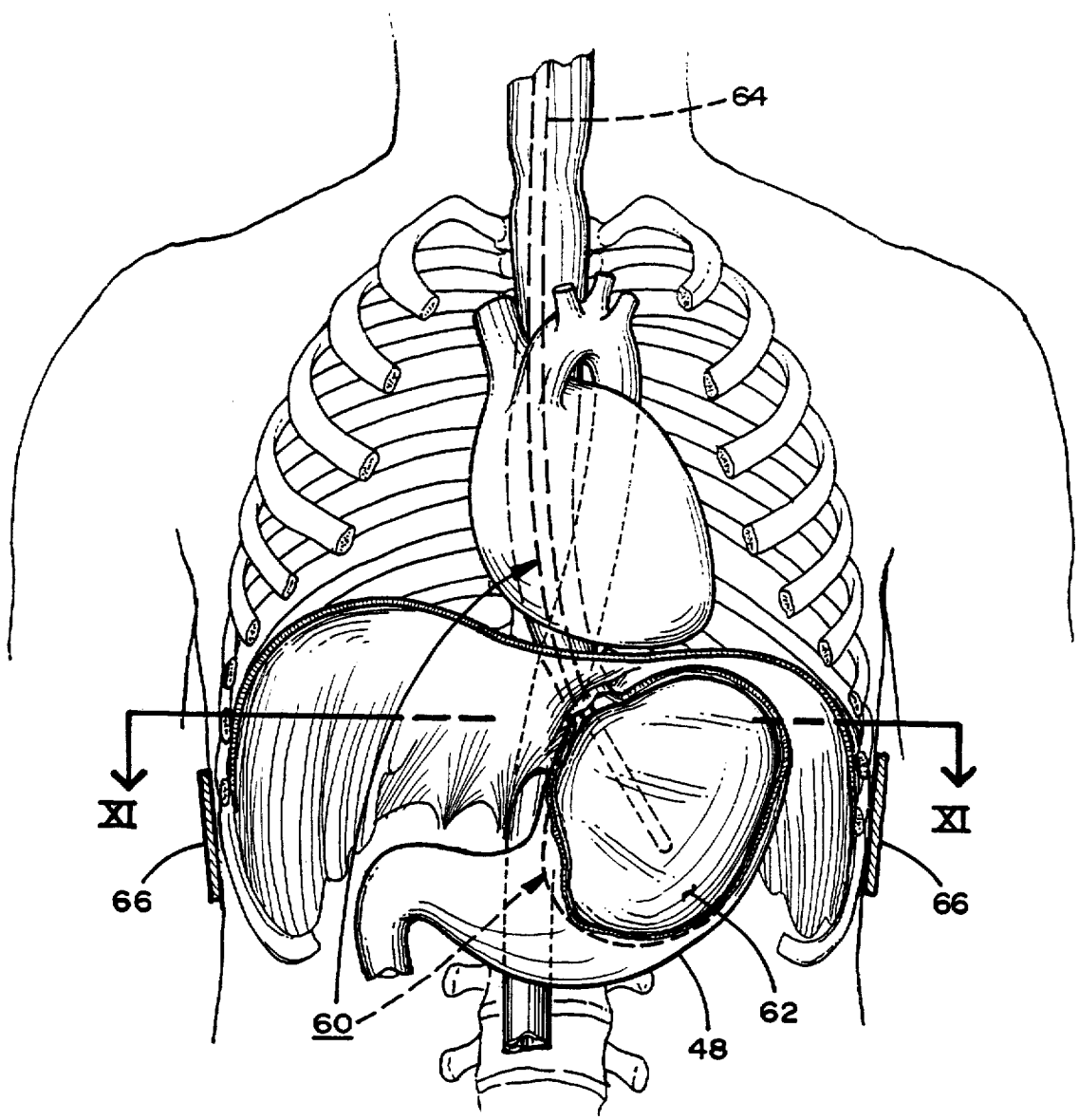
FIG. 9 is the same view as FIG. 1 illustrating an alternative embodiment of a non-invasive apparatus for at least partially occluding the descending aorta of a patient being used to enhance cerebral and myocardial perfusion in a patient or treating shock in a patient.

With apparatus 52 positioned in the patient, as illustrated in FIG. 6, inflation mechanism 58 is actuated in order to inflate inflatable member 54 in the patient's stomach 48. Traction is then applied to handgrip 59, as illustrated in FIG. 6, which applies a force F with inflatable member 54 posteriorly-laterally in the direction of the patient's descending aorta to partially or completely occlude the descending aorta, as illustrated in FIG. 8.

Because of its size, inflatable member 54 can only be properly inflated in the patient's stomach. Furthermore, once inflated in the patient's stomach, proper positioning of the inflatable member is readily achieved by the initial movement caused by the traction force F applied to handgrip 59 which draws the inflatable member to the wall of the stomach at the esophageal-gastric junction. Further traction force draws the inflatable member upwardly and posteriorly which is the direction necessary to impinge the descending aorta. Substantially completely occluding the patient's descending aorta requires extensive movement of an extensive portion of a wall of this artery against an extensive resistant force. The descending aorta is a main artery of the body. As such, it is a large vessel as can be seen in FIGS. 1–4. It is pressurized by the heart to a pressure that may extend over 200 millimeters of mercury, or approximately four pounds per square inch. Therefore, in order to substantially completely occlude the descending aorta, the device must overcome this pressure. Furthermore, the aorta is a muscular structure having muscle tone which affords rigidity to the structure. Therefore, the descending aorta has a stiffness which resists crushing thereof. While less than the pressure of the fluid in the descending aorta, this muscle tone adds appreciably to the force required to substantially completely occlude the descending aorta. In the illustrated embodiment, force sufficient to partially or completely occlude the aorta is achieved with inflatable member 54 being a balloon made of a suitable medical grade material, such as PPT, Mylar, or the like, and having a surface with a diameter preferably of between approximately 1 and approximately 6 inches and most preferably between approximately 2 and approximately 4 inches. Elongated member 56 has sufficient strength to allow sufficient force to be transmitted from handgrip 59 to inflatable member 54 to impart sufficient force to the surface of inflatable member 54 to partially or completely occlude the aorta.

Figure 10:
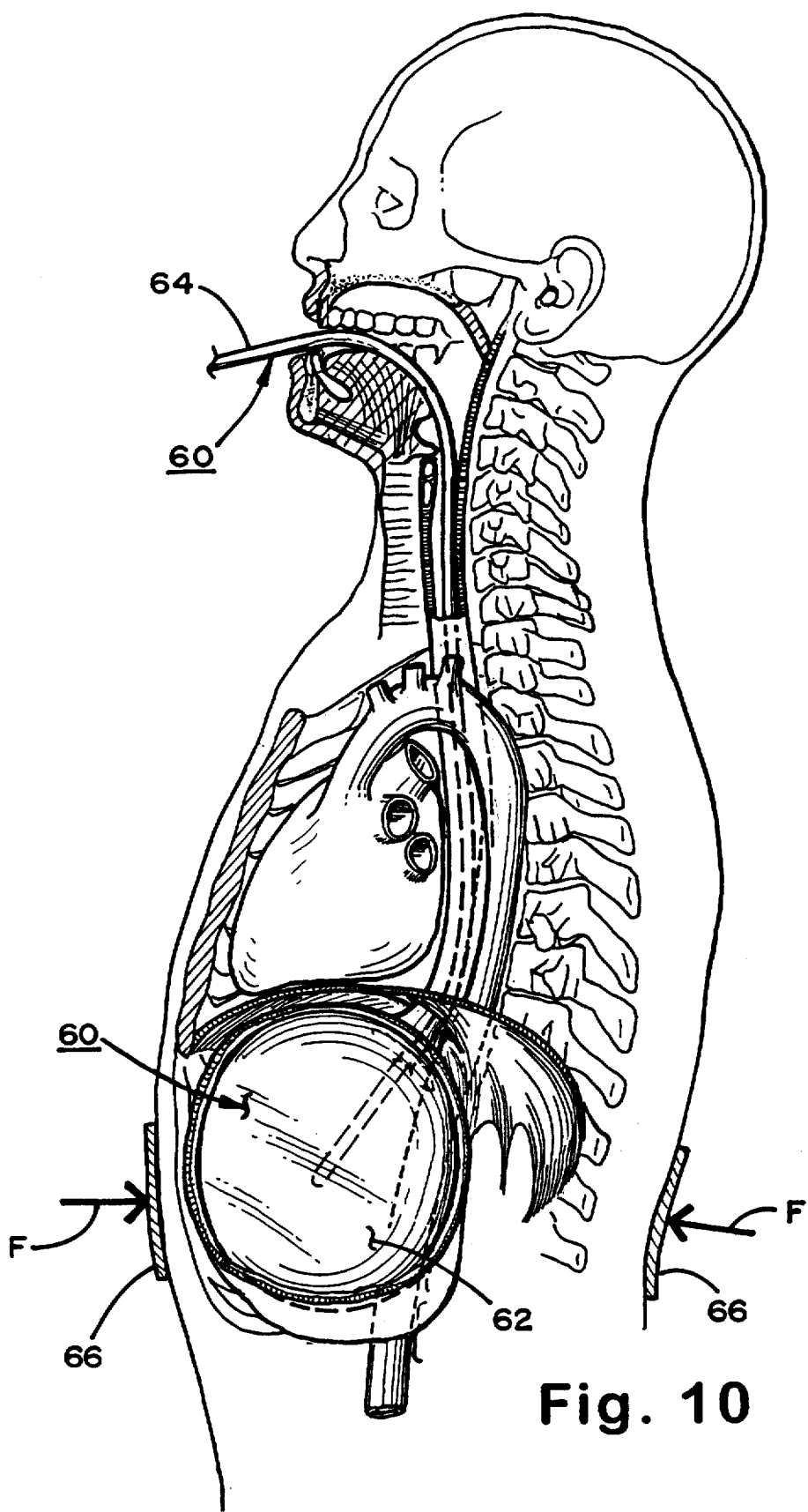
FIG. 10 is the same view as FIG. 2 of the method and apparatus illustrated in FIG. 9.
Figure 11:
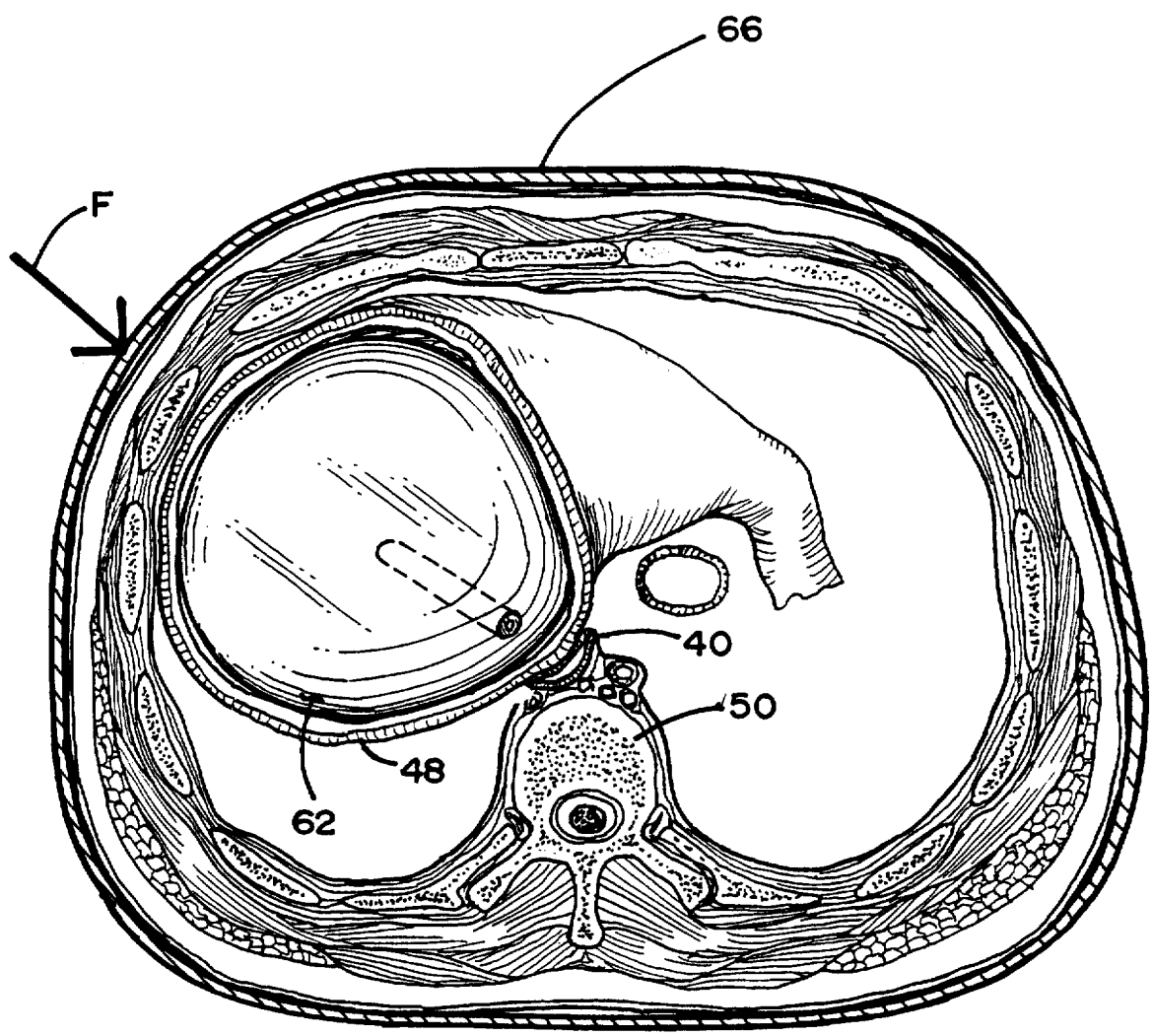
FIG. 11 is a sectional view taken along the lines XI—XI in FIG. 9.
Figure 13:
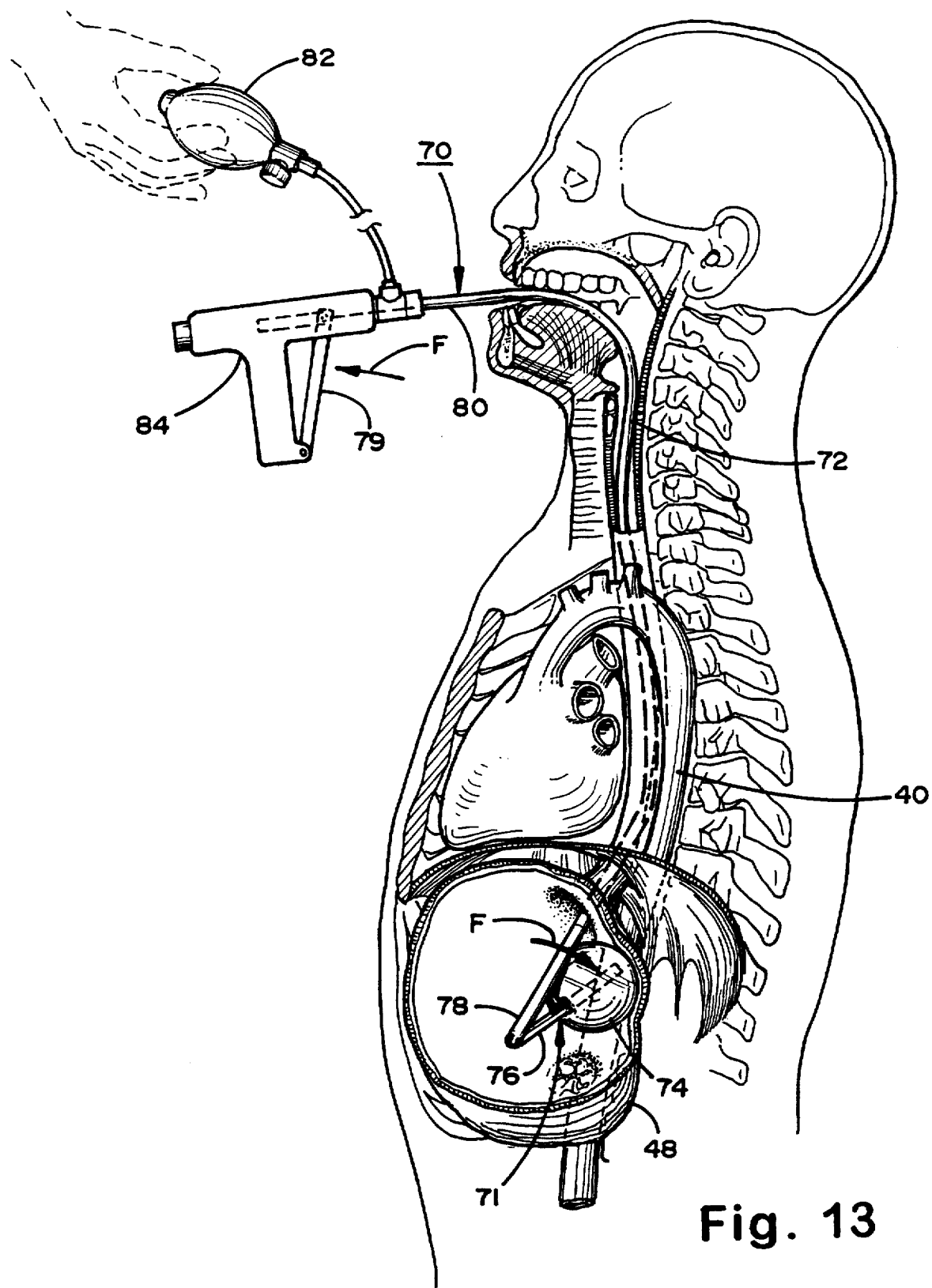
FIG. 13 is the same view as FIG. 2 illustrating the apparatus in FIG. 12 being used to enhance cerebral and myocardial perfusion in a patient or to treat shock in a patient.
Figure 14:
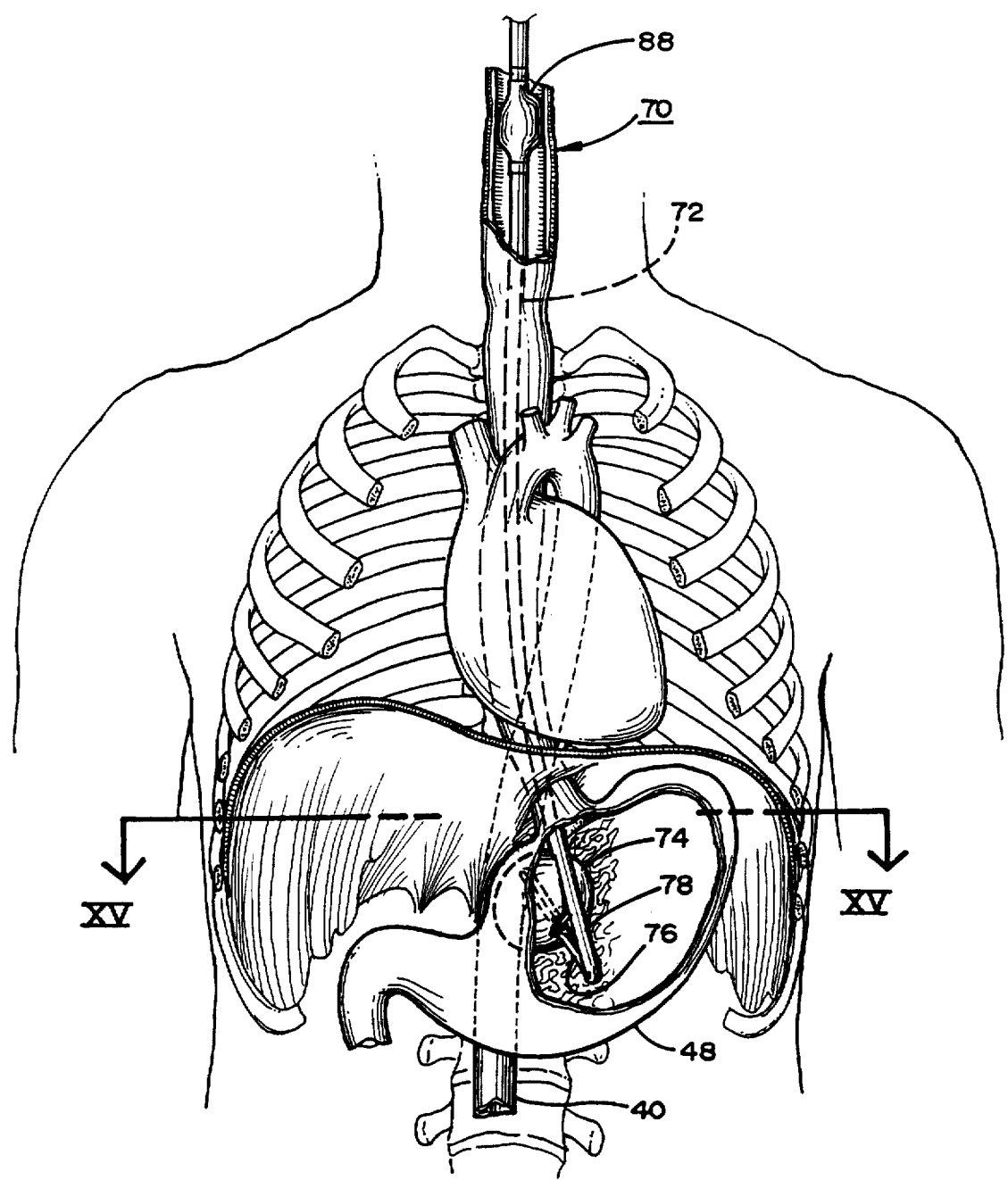
FIG. 14 is the same view as FIG. 1 of the method illustrated in FIG. 13.

In another embodiment of a non-invasive apparatus 60 for at least partially occluding the descending aorta of a patient, an inflatable member 62 is positioned in stomach 48 by a positioning member 64 and an inflation mechanism, similar to 58, is provided in order to inflate inflation member 62. With inflation member 62 fully inflated, a displacement mechanism 66 displaces inflatable member 62 posteriorly in the direction of the patient's descending aorta thereby producing a force posteriorly in the direction of the patient's descending aorta sufficient to partially or completely occlude the descending aorta. In this embodiment, displacement mechanism 66 applies a force from external the patient to inflatable member 62. Inflatable member 62 is of a sufficient size such that the force, which is transmitted through the patient's abdominal wall, is transmitted through the inflatable member in order to partially or completely occlude the descending aorta as best illustrated in FIG. 11. In the illustrated embodiment, the displacement mechanism 66 is a strap placed around the abdomen such that a tightening of the strap applies the force F illustrated in FIGS. 10 and 11.

In order to properly locate displacement mechanism 66, the lower tip of the sternum is identified and the displacement mechanism applied to the patient in a manner which applies a force posteriorly just below the sternum. Because the diaphragm is attached at the sternum, applying a force F just below the sternum will ensure that the force is applied to the stomach and thereby transmitted posteriorly to impinge upon the aorta.

In the illustrated embodiment, inflatable member 62, when inflated, has a diameter of between approximately 10 and approximately 30 inches and most preferably between approximately 15 and approximately 22 inches. While displacement mechanism 66 is illustrated as a belt, other mechanisms, including pneumatic actuators, manual compression, and the like, can be utilized in order to apply force F externally of the patient. Also, the force F may be applied in synchronism with the patient's ventricular contractions in order to counter-pulse the aorta during ventricular diastole such as by using a pneumatic CPR device operated from the cardiac signal in the manner described in the '776 patent. One such CPR device is the THUMPER® resuscitator marketed by Michigan Instruments, Inc. of Grand Rapids, Mich.

In another embodiment illustrated in FIGS. 12–15, a non-invasive apparatus 70 for at least partially occluding the descending aorta of a patient includes an elongated member 72 which is configured to extend through the patient's esophagus 42 and a moveable portion 71 defined by an inflatable member 74 displaceable from elongated member 72 in the patient's stomach 48 by a displacement mechanism 76 which mechanically displaces inflatable member 74 from proximal end 78 of the elongated member.

In the illustrated embodiment, displacement mechanism 76 is a lever which is pivoted outwardly by an actuator 79 positioned at a distal end 80 of elongated member 72. An inflation mechanism 82 is also provided at distal end 80 of elongated member 72 in order to selectively inflate inflatable member 72. In operation, with inflatable member 74 in a non-inflated state and with actuator 79 not being actuated, elongated member 72 is inserted in the patient's esophagus, nasally or orally, until proximal end 78 is positioned within the stomach. This can be accomplished utilizing conventional techniques for positioning nasal gastric tubes in the patient. Namely, markings can be provided on elongated member 72 and, prior to insertion of apparatus 70 in the patient, the apparatus can be compared with the external physiology of the patient in order to determine the amount of insertion necessary in order to position proximal end 78 in the patient's stomach.

Figure 15:
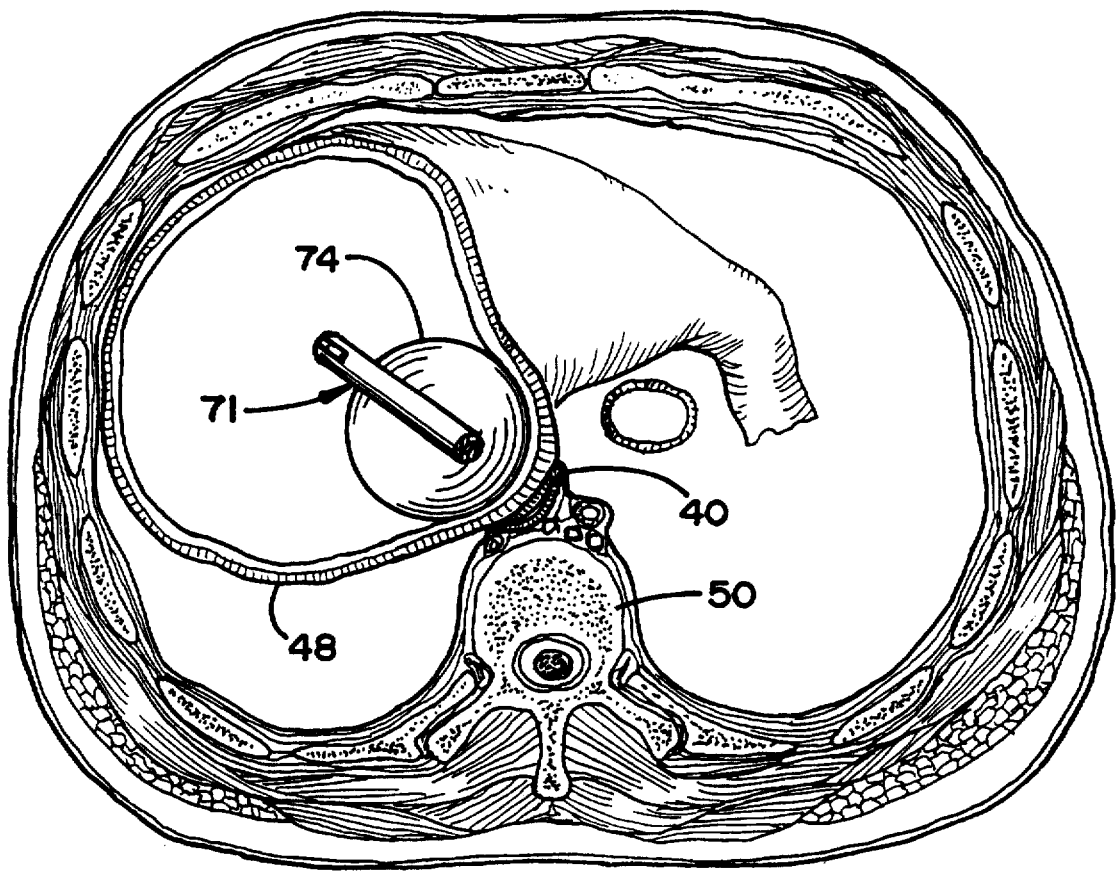
FIG. 15 is a sectional view taken along the lines XV—XV in FIG. 14.

After the apparatus is properly positioned, inflation mechanism 82 is actuated in order to inflate inflatable member 74 and thereby create an enlarged surface for impingement with the descending aorta. With the inflatable member inflated, actuator 79 is actuated by hand manipulation in order to cause displacement member 76 to displace inflatable member 74 posteriorly with a sufficient force to at least partially occlude the descending aorta as illustrated in FIG. 15. In order to ensure that operation of actuator 79 will cause displacement mechanism 76 to displace inflatable member 74 in the proper direction, a radially positioning device 84, which is illustrated as a pistol grip handle, may be provided such that with the radial positioning device in a particular orientation with respect to the patient, displacement mechanism 76 and inflatable member 74 are oriented in a manner which will produce the desired movement of the inflatable mechanism upon movement of the displacement mechanism. In the illustrated embodiment, inflatable member 74 has a diameter, when inflated, preferably of between approximately 1.5 and approximately 10 inches and most preferably between approximately 2 and approximately 4 inches.

Figure 16:
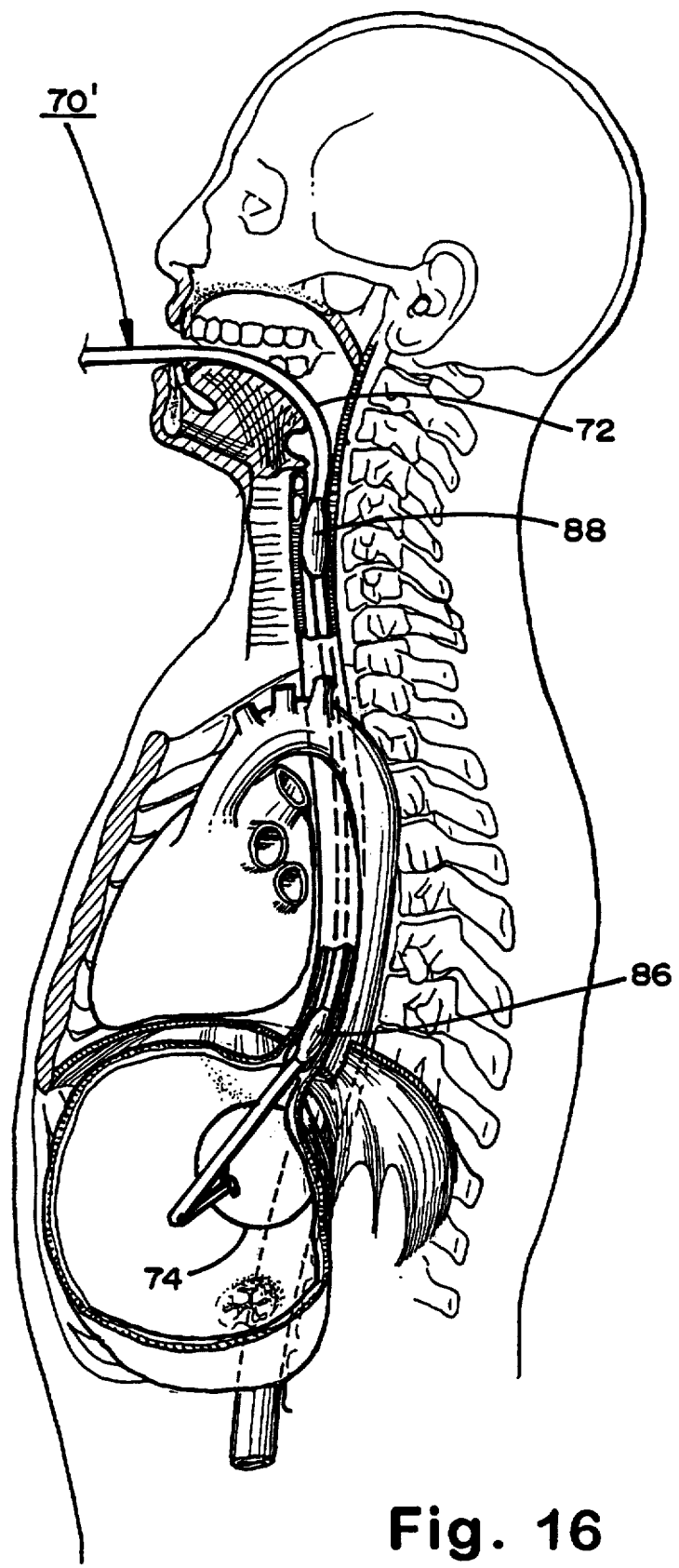
FIG. 16 is the same view as FIG. 2 illustrating a modification to the embodiment of the method and apparatus in FIGS. 12 and 13.
Figure 19:
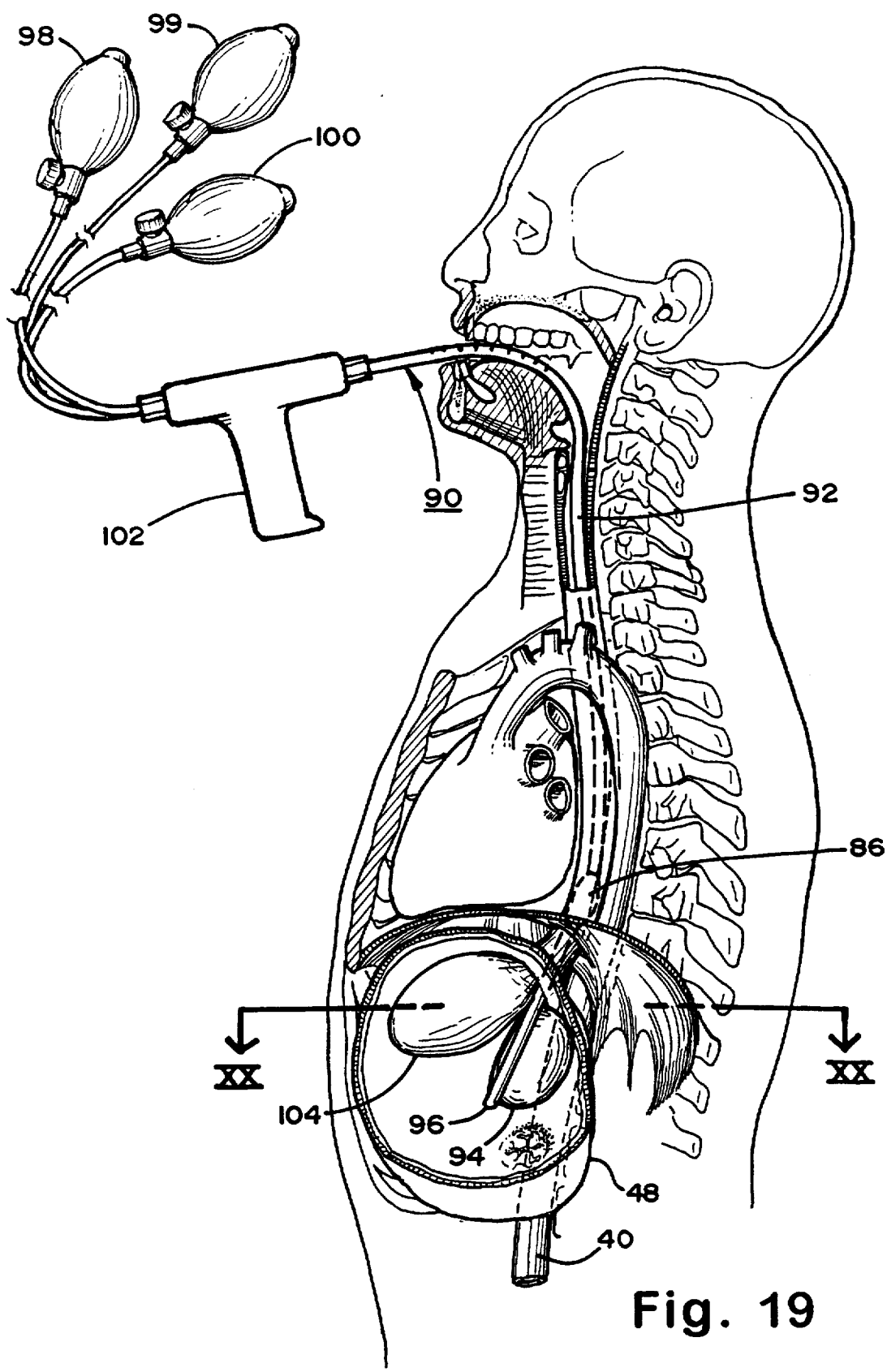
FIG. 19 is the same view as FIG. 2 illustrating the apparatus in FIG. 17 used to enhance cerebral and myocardial perfusion to treat shock in a patient.

A modified non-invasive apparatus 70' for at least partially occluding the descending aorta of a patient is illustrated in FIG. 16. Apparatus 70' is similar to apparatus 70 except that it includes an anchor member 86 to anchor elongated member 72 in a lower portion of esophagus 42 and a device 88 on elongated member 72' located at an upper portion of esophagus 42. Anchor 86 may be, by way of example, an inflatable cuff and is for the purpose of imparting somewhat rigid positioning of elongated member 72' in the esophagus in order to increase the force that inflatable member 74 is capable of providing posteriorly in order to more effectively partially or completely occlude the patient's descending aorta. Device 88, which may be an inflatable cuff, is to seal the esophagus and prohibit the contents of the stomach from flowing upwardly through the throat and to otherwise provide proper airway management.

Figure 20:
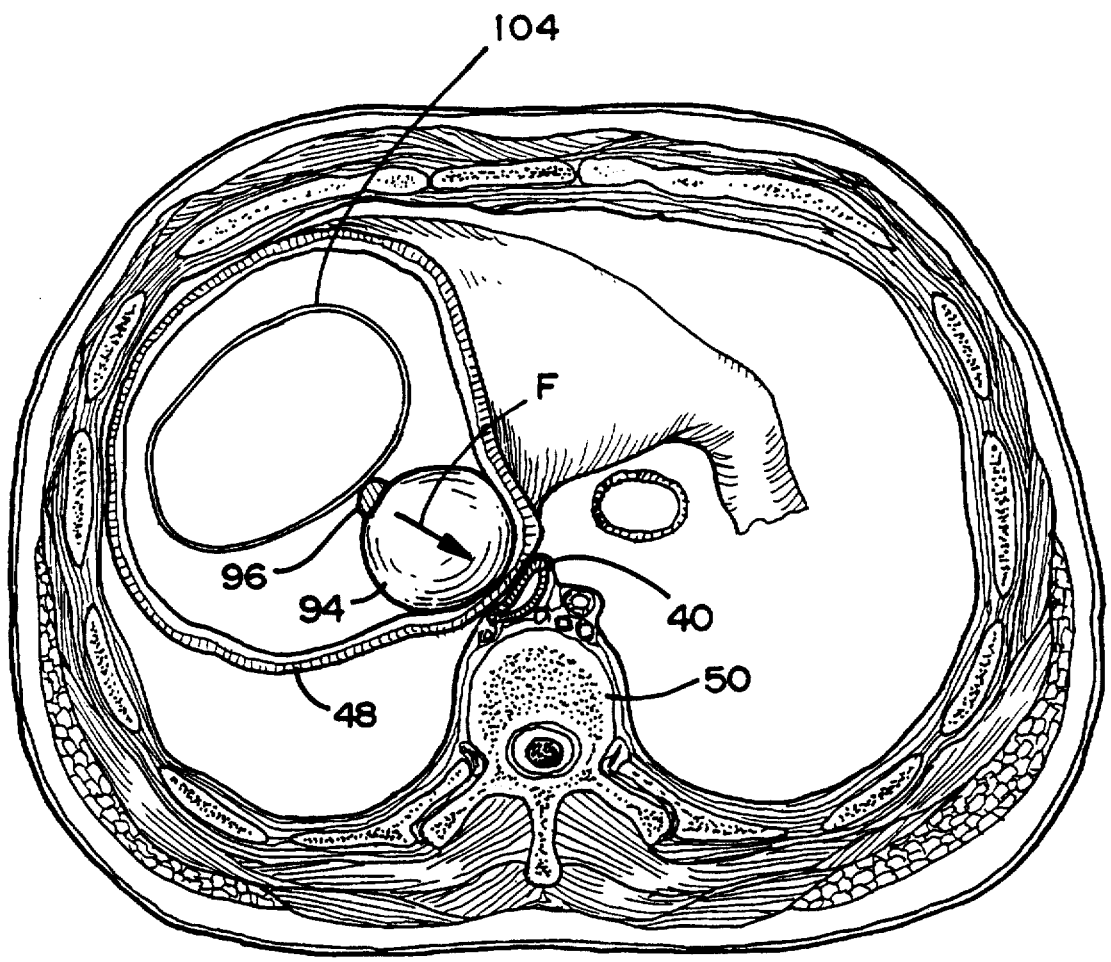
FIG. 20 is a sectional view taken along the lines XX—XX in FIG. 19.

Another embodiment of a non-invasive apparatus 90 for at least partially occluding the descending aorta of a patient includes an elongated member 92 and an inflatable member 94 which produces a force posteriorly in the direction of the patient's descending aorta sufficient to cause partial or complete occlusion of the patient's descending aorta (FIGS. 17–20). Inflatable member 94 is joined with an elongated member 92 at a reaction surface, or portion, 96 of the elongated member. Reaction portion 96 provides a stable platform against which the inflatable member 94 expands when inflated in order to produce a force posteriorly in the direction of the patient's descending aorta. Apparatus 90 may include another anchor device, such as an inflatable member 104, which is positioned within the stomach of the patient and provides an additional anchor for reaction portion 96. In this manner, with inflatable member 104 inflated by an inflation mechanism 106, reaction portion 96 is stabilized to allow greater force to be transmitted posteriorly by the impingement surface of inflatable member 94. In this manner, when inflatable member 94 is inflated by actuation of inflation mechanism 98, the expansion of its surface provides a force posteriorly in the direction of the patient's descending aorta sufficient to cause substantially complete occlusion of the patient's descending aorta as illustrated in FIG. 20.

Apparatus 90 additionally includes an inflation mechanism 98 for selectively inflating inflatable member 94, a second inflation mechanism 99 for selectively inflating an anchor member 86 and an airway control device 88 and a third inflation mechanism 100 for selectively inflating anchor 104. Apparatus 90 may further include a radial-positioning device 102 in the form of a pistol grip, or the like, in order to provide for radial positioning of inflatable member 94 and an indication of the positioning thereof.

Figures 21, 24:
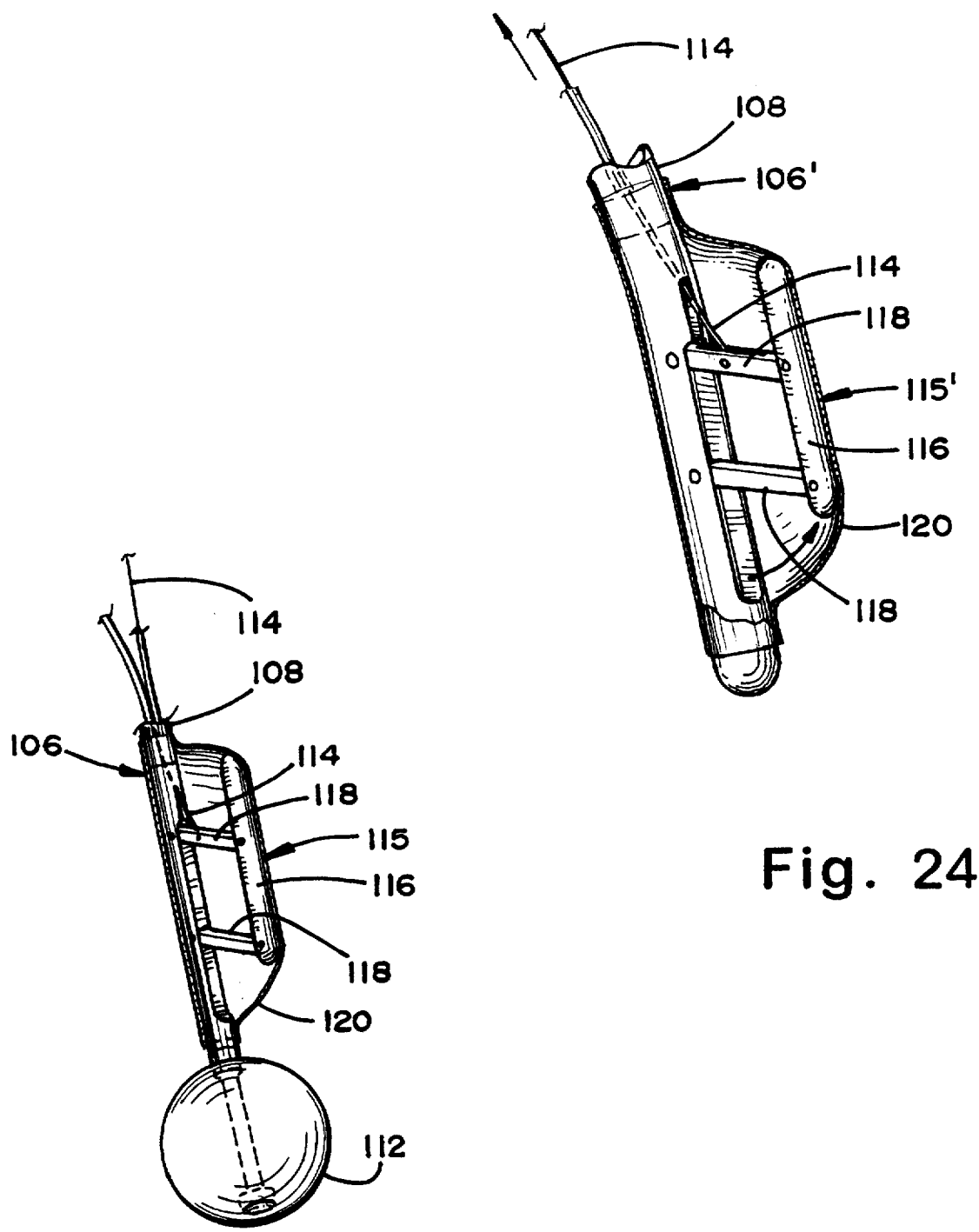
FIG. 21 is an enlarged partial perspective view of another alternative embodiment of a non-invasive apparatus for at least partially occluding the descending aorta of a patient.
FIG. 24 is an enlarged partial perspective view of another alternative embodiment of a non-invasive apparatus for at least partially occluding the descending aorta of a patient.
Figure 22:
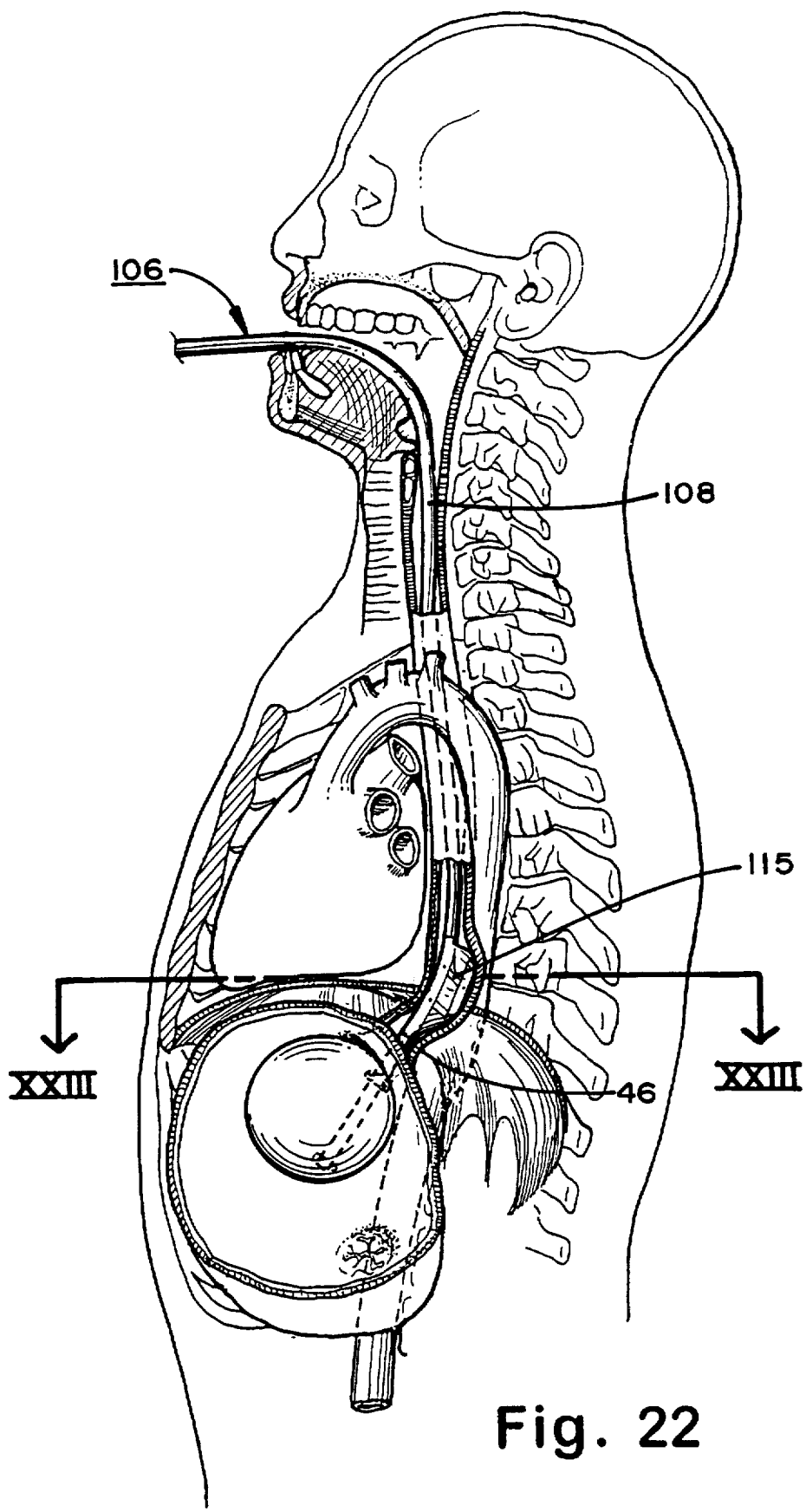
FIG. 22 is the same view as FIG. 2 illustrating the apparatus in FIG. 21 used to enhance cerebral and myocardial perfusion or to treat shock in a patient.
Figure 23:
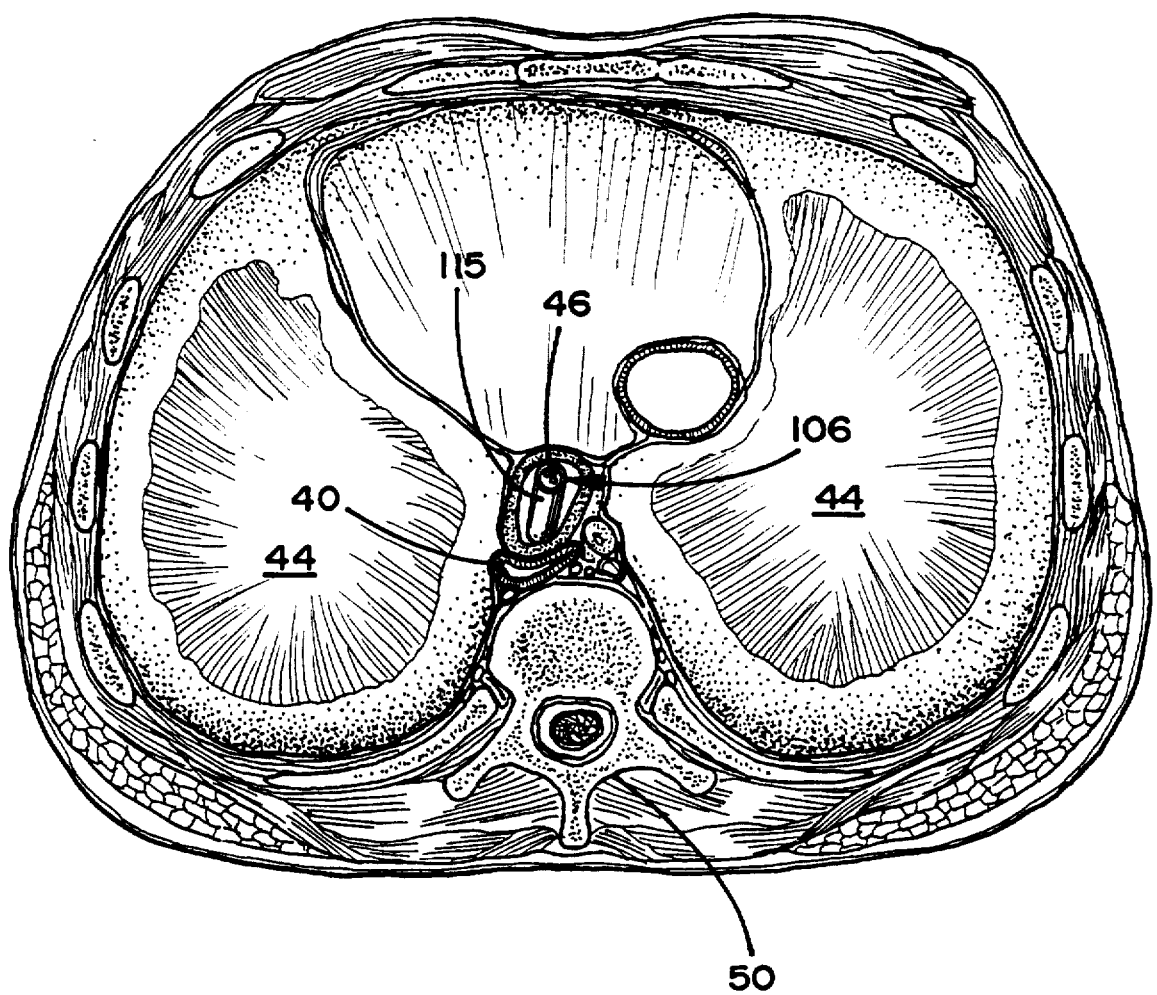
FIG. 23 is a sectional view taken along the lines XXIII—XXIII in FIG. 22.

An alternative embodiment of a non-invasive apparatus 106 for at least partially occluding the descending aorta of a patient includes a tubular member 108 having a selectively movable portion 115 which is positioned adjacent the patient's esophageal-gastric junction when tubular member 108 is positioned in the patient's esophagus (FIGS. 21–23). Apparatus 106 may include an anchor balloon 112 positionable in the patient's stomach in order to stabilize apparatus 106 within the patient. With elongated member 108 positioned within the patient's esophagus, a displacement mechanism including a cable 114, or the like, which is selectively actuatable causes movable portion 115 to move laterally a sufficient distance in order to partially or completely occlude the patient's descending aorta. In the illustrated embodiment, selectively movable portion 115 includes a displacement surface 116 having a sufficient area to substantially completely occlude the patient's descending aorta and a pair of parallel linkages 118 which support displacement surface 116 in a parallel relationship with tubular member 108 as surface 116 is displaced laterally therefrom. Apparatus 106 may additionally include a sheath 120 covering displacement surface 116.

As best seen in FIGS. 22 and 23, actuation of cable 114 by a displacement mechanism, or actuator, similar to 79, causes moveable portion 115 to be laterally displaced from tubular member 108 and thereby applying a force in the direction of the patient's descending aorta sufficient to cause partial or complete occlusion of the patient's descending aorta. Moveable portion 115 is laterally displaceable preferably of between approximately 1 and approximately 4 inches and most preferably of between approximately 2 and approximately 3 inches.

Figure 25:
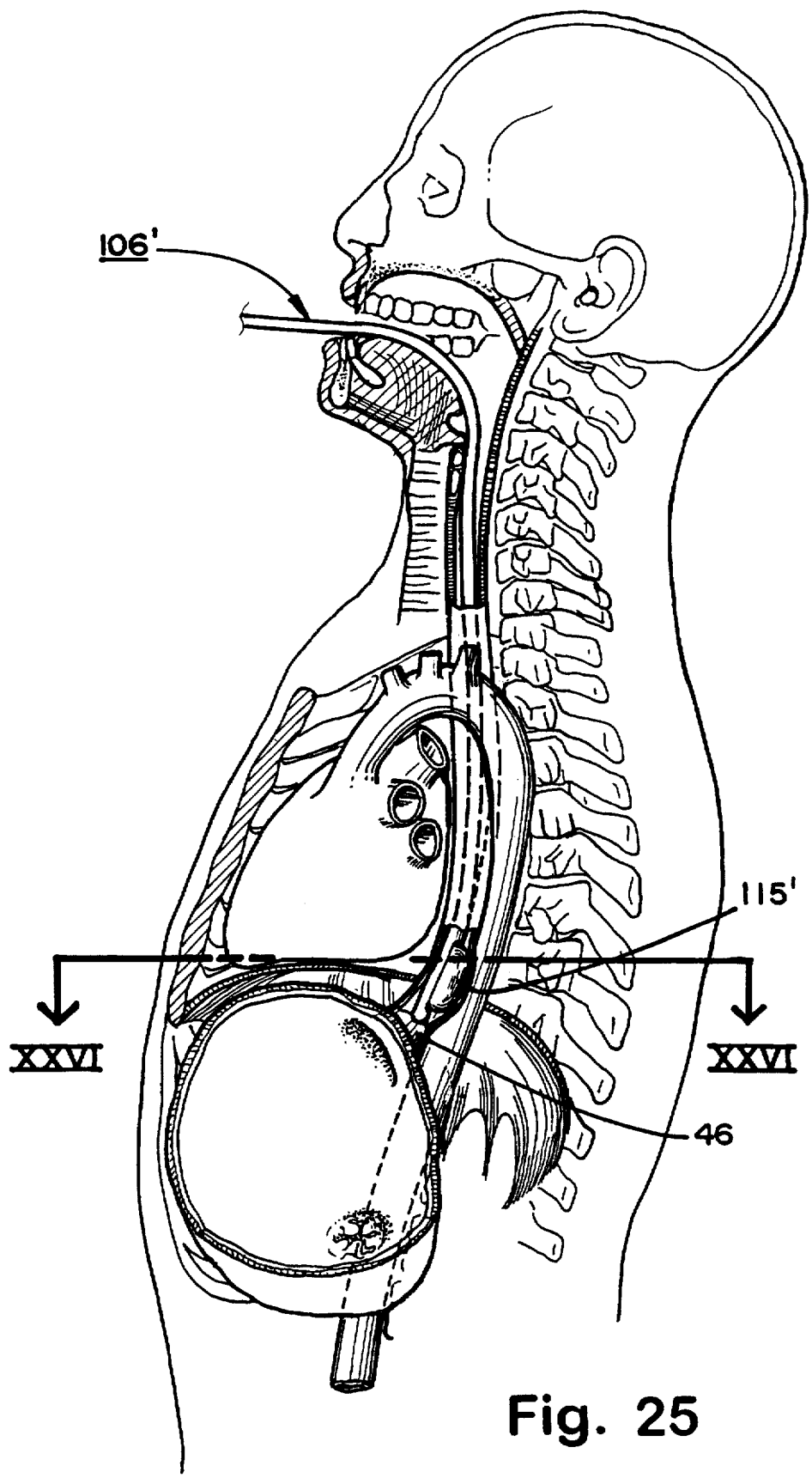
FIG. 25 is the same view as FIG. 2 illustrating the apparatus in FIG. 24 used to enhance cerebral and myocardial perfusion or to treat shock in a patient.
Figure 26:
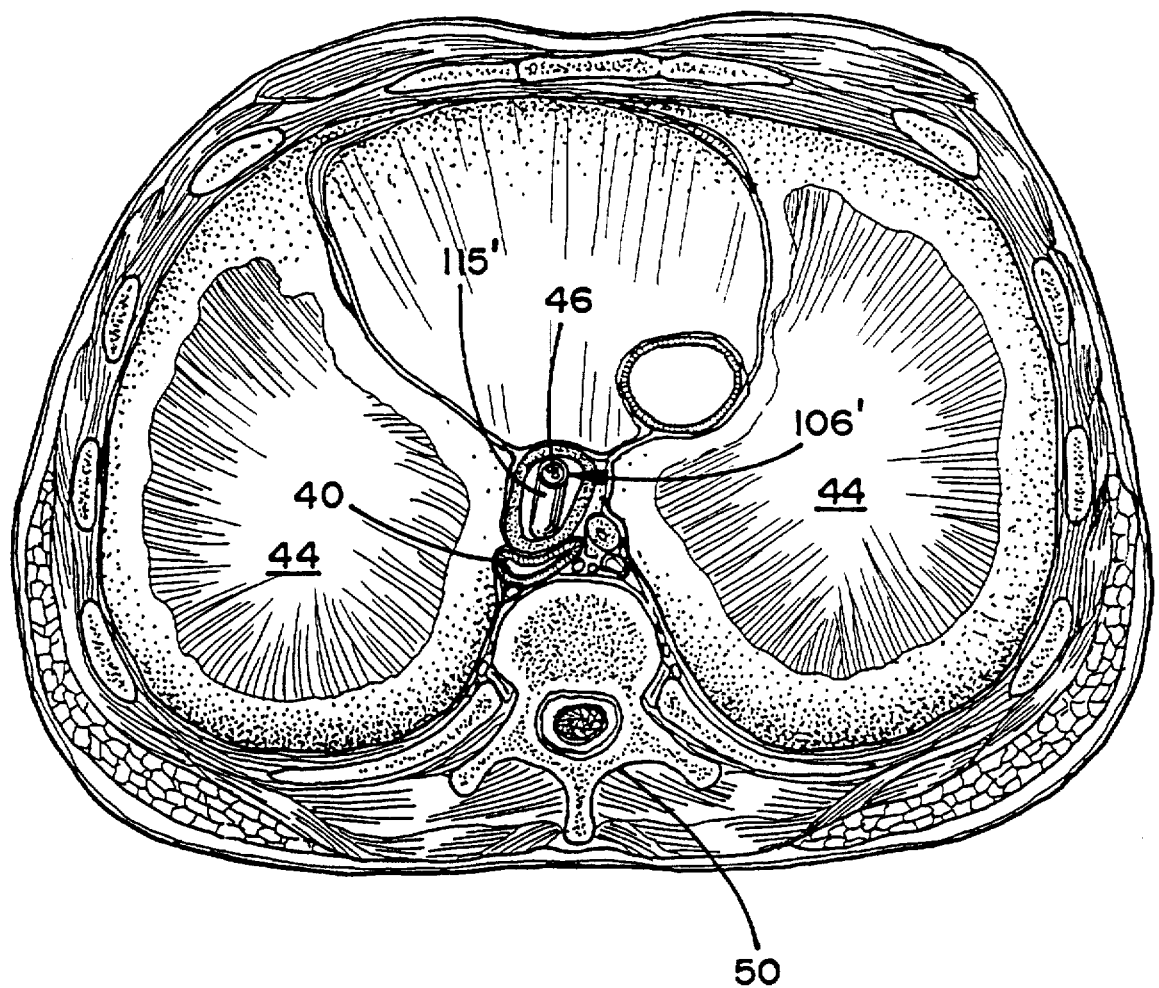
FIG. 26 is a sectional view taken along the lines XXVI—XXVI in FIG. 25.

Another embodiment of a non-invasive apparatus 106' for at least partially occluding the descending aorta of a patient is similar to apparatus 106 except that it does not include an anchor balloon in the patient's stomach but is otherwise the same as apparatus 106 (FIGS. 24–26).

Figures 27, 30:
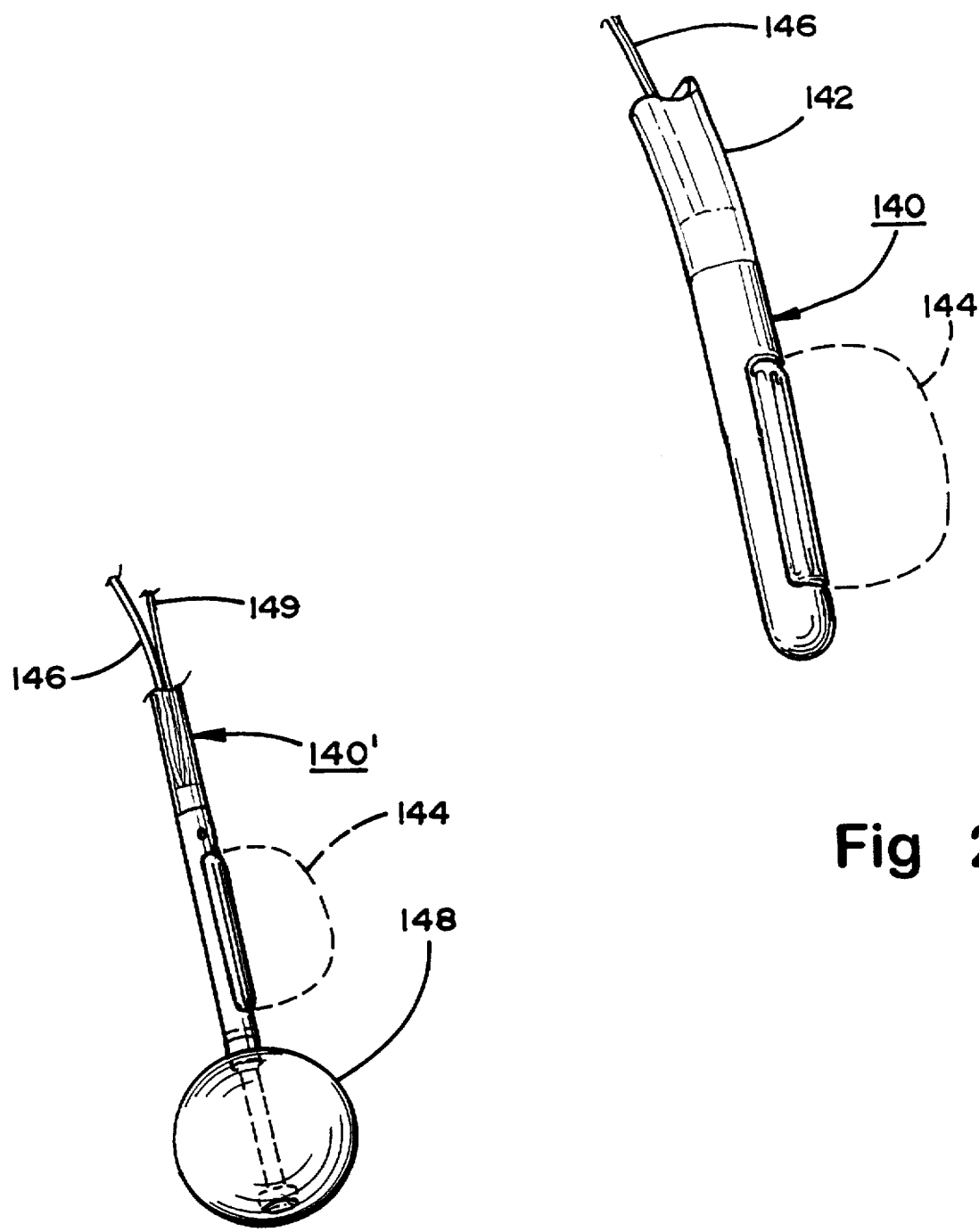
FIG. 27 is an enlarged partial perspective view of another alternative embodiment of a non-invasive apparatus for at least partially occluding the descending aorta of a patient.
FIG. 30 is an enlarged partial perspective view of another alternative embodiment of a non-invasive apparatus for at least partially occluding the descending aorta of a patient.
Figure 28:
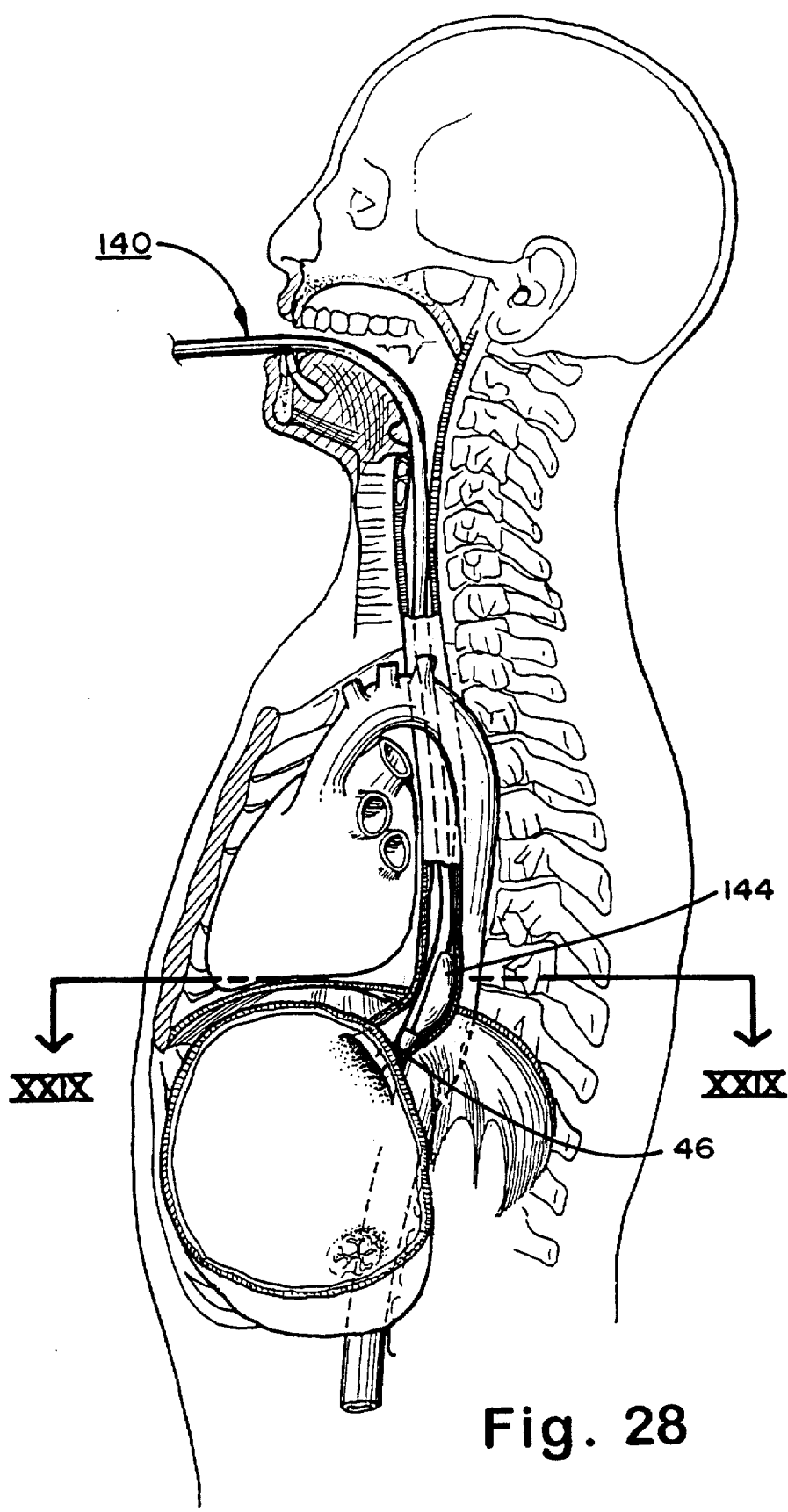
FIG. 28 is the same view as FIG. 2 illustrating the apparatus in FIG. 27 used to enhance cerebral and myocardial perfusion or to treat shock in a patient.
Figure 29:
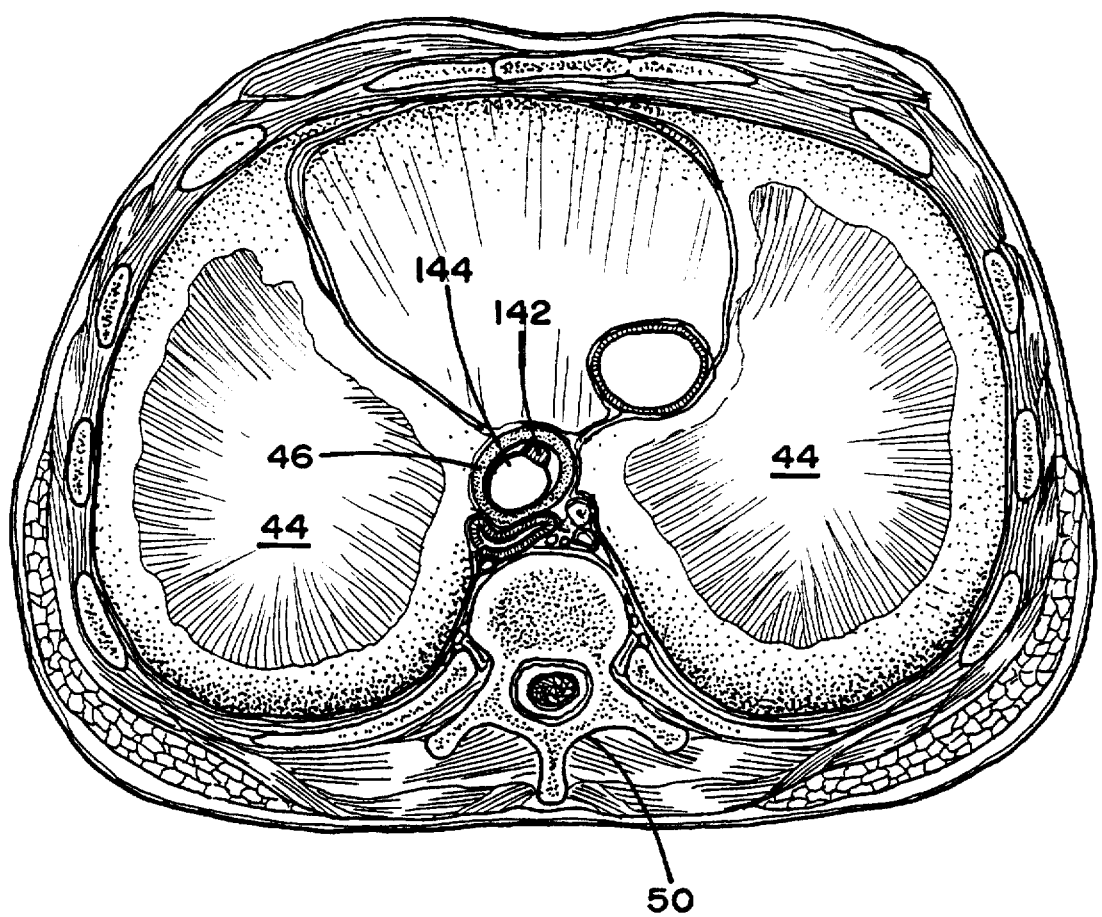
FIG. 29 is a sectional view taken along the lines XXIX—XXIX in FIG. 28.

Another alternative embodiment 140 of a non-invasive apparatus for at least partially occluding the descending aorta of a patient includes a tubular member 142 having a selectively moveable portion 144 which is positioned adjacent the patient's esophageal-gastric junction when tubular member 142 is positioned in the patient's esophagus (FIGS. 27–29). Selectively moveable portion is an inflatable member, such as an inflatable cuff or balloon, which is selectively inflatable by an inflation mechanism through a tube 146. Inflatable member 144 is preferably constructed to inflate primarily in a posterior direction, as illustrated, but may also be a uniform member which inflates in all directions and thereby applies a force posteriorly in the direction of the descending aorta.

An alternative embodiment 140' of a non-invasive apparatus for at least partially occluding the descending aorta of a patient is the same as apparatus 140 except that it also includes an anchor balloon 148 positionable in the patient's stomach and an inflation mechanism which selectively inflates the balloon through a tube 149.

Figures 31, 32:
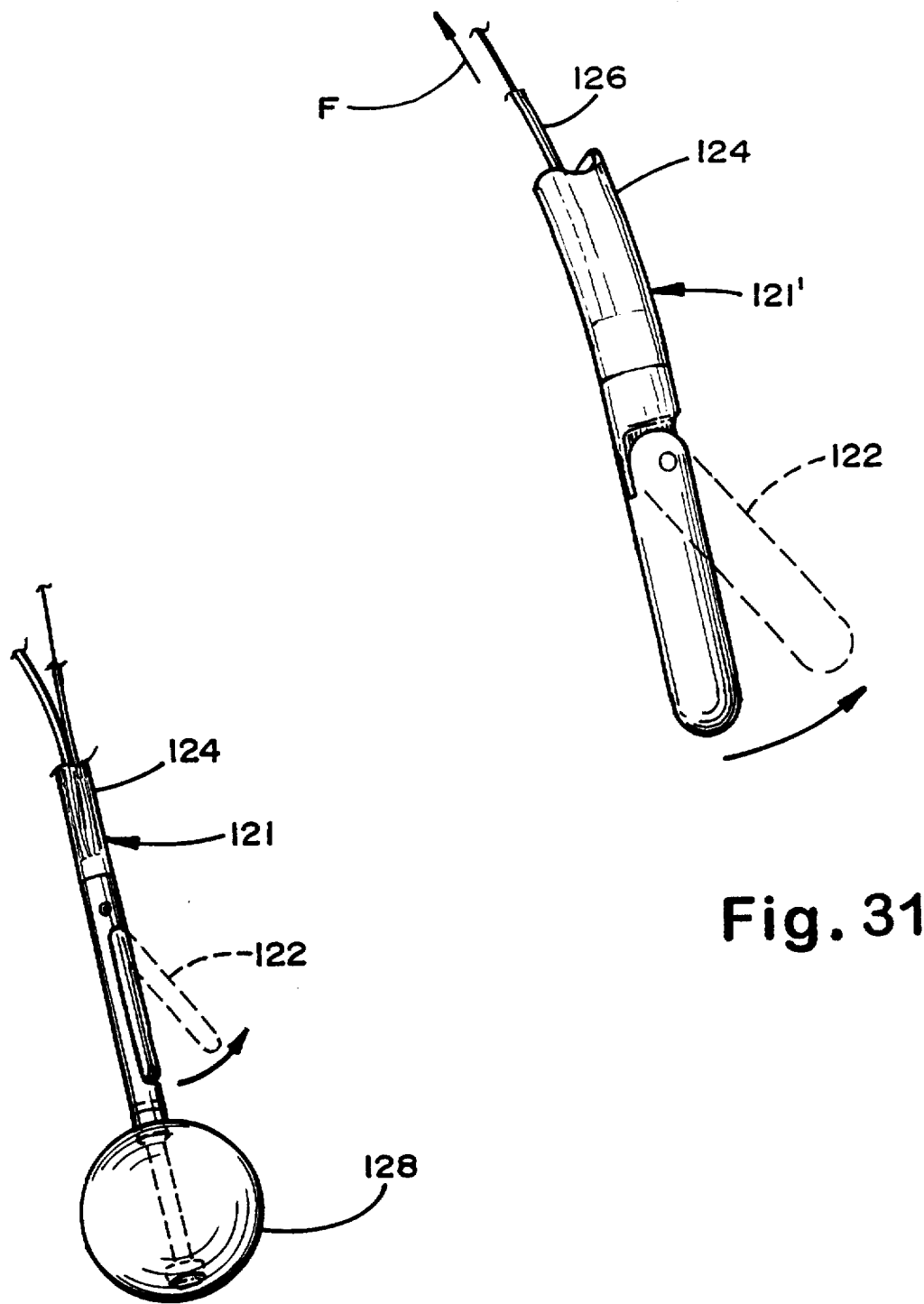
FIG. 31 is an enlarged partial perspective view of another alternative embodiment of a non-invasive apparatus for at least partially occluding the descending aorta of a patient.
FIG. 32 is an enlarged partial perspective view of yet another alternative embodiment of a non-invasive apparatus for at least partially occluding the descending aorta of a patient.

Other embodiments of a non-invasive apparatus for at least partially occluding the descending aorta of a patient will suggest themselves to the skilled artisan. For example, in FIGS. 31 and 32, a non-invasive apparatus 121, 121' is provided in which a selectively moveable portion 122, 122' is in the form of a lever which pivots about an elongated member 124, 124' by a displacement mechanism including a cable 126, 126'. The displacement mechanism displaces moveable portion 122, 122' in the direction of the patient's descending aorta, when tubular member 104, 104' is positioned in the patient's esophagus, with a force sufficient to cause partial or complete occlusion of the patient's descending aorta. Apparatus 121 additionally includes an anchor balloon 128 positioned in the patient's stomach for anchoring apparatus 121 when balloon 128 is inflated.

The effectiveness of a non-invasive apparatus and method according to the invention can be demonstrated by actual studies performed on a swine model in which fibrillation is induced. By reference to FIG. 33, aortic arch pressure is illustrated by graph 130 and right atrial pressure is illustrated by graph 132 after fibrillation is induced in the patient and a conventional CPR protocol is performed. The CPR protocol pictured involves a series of five chest compressions followed by a pause during which ventilation occurs as can be observed in graph 130. A non-invasive apparatus according to the invention is utilized to at least partially occlude the descending aorta at point A which, in the illustrated embodiment, is more than 17 minutes following inducement of fibrillation. It can be seen that, following application of the invention at point A, the aortic arch pressure begins to increase, while little change occurs in the diastolic right atrial pressure. This results in a significant increase in coronary and cerebral perfusion pressure. Significantly, such increase in perfusion pressure occurred more than 17 minutes after onset of fibrillation. This is significant because, as is known in the art, the metabolic state of the myocardium and peripheral vascular resistance decreases with patient arrest time. Furthermore, this observed increase after application of the invention occurs without the use of intravenously administered adrenergic agents such as epinephrine. Therefore, the ability to increase perfusion pressure after a relatively long downtime is significant.

Figure 34:
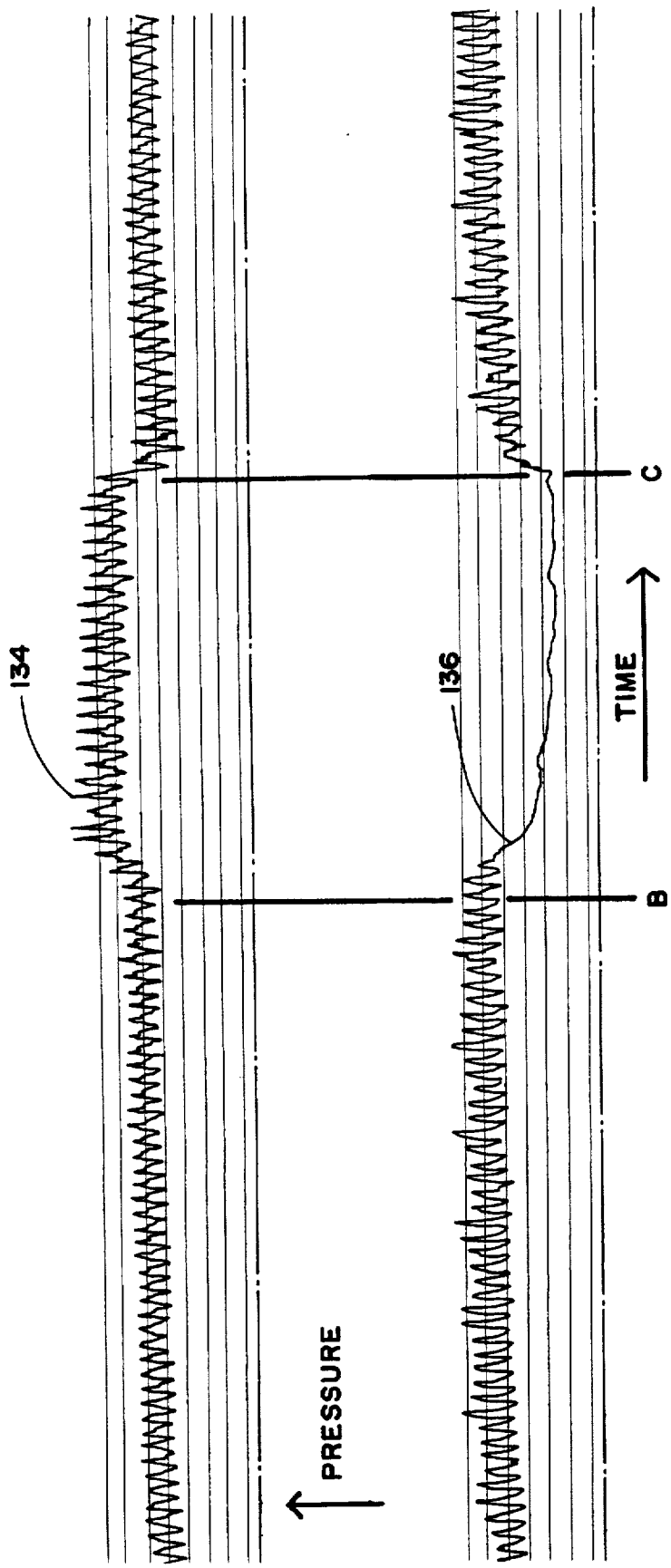
FIG. 34 is a diagram illustrating increases in myocardial and cerebral perfusion pressure in a swine model treated according to the invention.

FIG. 34 illustrates an aortic arch pressure graph 134 and femoral artery pressure graph 136 in a swine patient in which a non-invasive apparatus according to the invention is utilized to occlude the descending aorta of the patient. At point B, the occlusion of the aorta results in a substantial increase in aortic arch pressure and a concurrent decrease in femoral artery pressure which represents the intravascular arterial pressure distal to the point of occlusion. This will naturally result in an increase in myocardial and cerebral perfusion as a result of the use of an apparatus according to the invention to perform a method according to the invention. Had the patient been hemorrhaging in the abdomen, activation of the device would have stopped this hemorrhaging while simultaneously increasing cerebral and myocardial perfusion. At point C, the apparatus is disengaged resulting in return of the femoral artery pressure in graph 136 and a decrease in aortic arch pressure in graph 134. This results in a lowering of myocardial and cerebral perfusion pressure.

Figure 33:
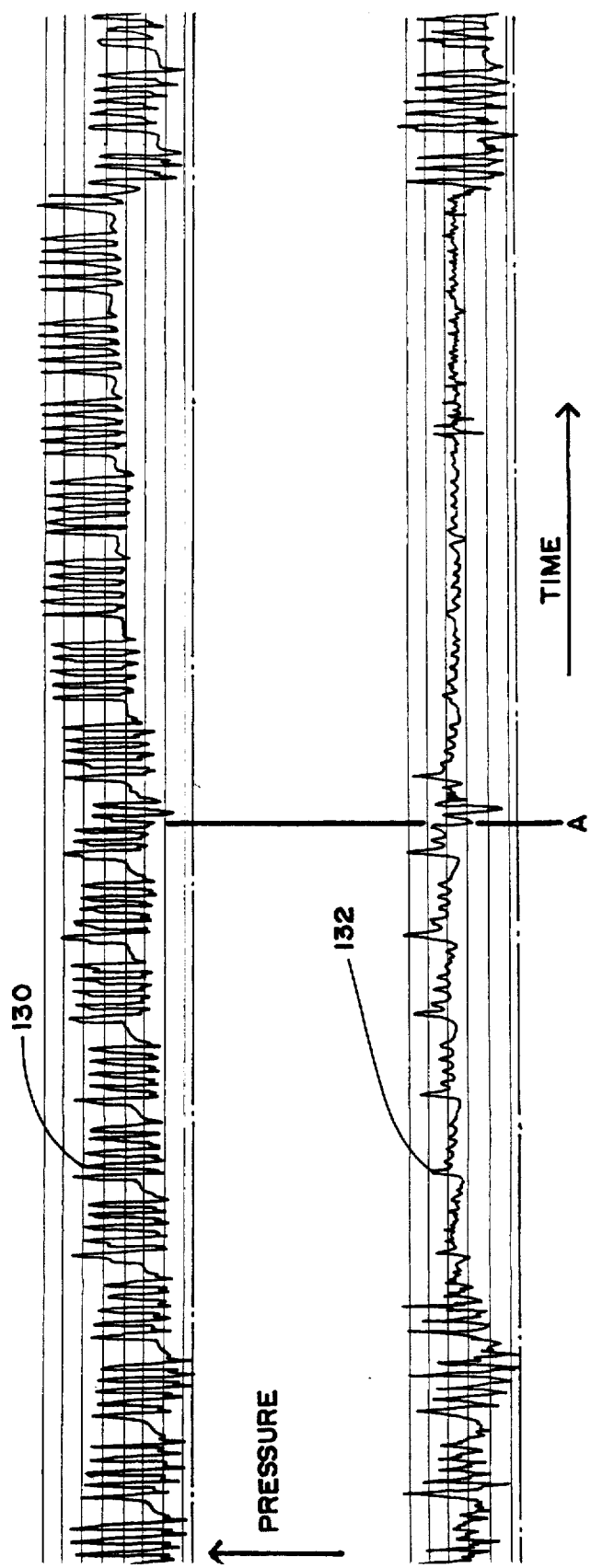
FIG. 33 is a diagram illustrating increases in myocardial and perfusion pressure in a swine model treated according to the invention.

The actual test results illustrated in FIGS. 33 and 34 demonstrate a diversion of blood flow from the tissue bed below the diaphragm to the myocardial and cerebral tissue beds above the diaphragm. This diversion of blood is proportional to the degree of occlusion of the aorta. Therefore, the increase in coronary and cerebral perfusion can be regulated if desired.

Thus, it is seen that the present invention provides hemorrhage control for the management of trauma and an inhibition of flow below the diaphragm to enhance coronary and cerebral perfusion particularly during cardiopulmonary resuscitation. Studies have shown that, although over half of the tissue beds are below the diaphragm, approximately two-thirds of bleeding that leads to hemorrhagic shock occurs below the diaphragm. Therefore, the ability to control bleeding below the diaphragm provides a significant advantage particularly in management of trauma. This is particularly useful in treating patients who have suffered abdominal injuries from knives and guns, blunt trauma from falls, explosions, motor vehicle accidents, complications due to the delivery of babies from subdiaphragmatic hemorrhaging and other vascular catastrophes below the diaphragm such as ruptured abdominal aortic aneurysms. The present invention is particularly useful in battlefield applications in which it is essential to be able to rapidly control life-threatening hemorrhage in a non-invasive manner in order to avoid immediate death and complications from infections and the like until definitive repair of injuries can take place. Additionally, the ability to perform this procedure rapidly and effectively reduces the exposure of the medical personnel to battlefield injuries.

Other changes and modifications in the specifically described embodiments can be carried out without departing from the principles of the invention. For example, electrodes can be applied to stomach balloons for use in cardiac pacing and defibrillation. Although balloons and cuffs may be inflated using air, other techniques involving hydraulic fluids and mechanical actuators may suggest themselves to those skilled in the art. Although inflatable devices are illustrated as spherical, other shapes could be used such as cylindrical, pill-shaped, and the like. Also, the various elements of each illustrated embodiment of the invention can be combined and substituted with other of the embodiments. The embodiments are provided in order to illustrate the invention and should not be considered limiting. Displacement in the direction of the patient's descending aorta in order to at least partially occlude the descending aorta can be performed in synchronism with the patient's ventricular contractions, as disclosed in the above-referred to '776 patent, in order to counter-pulse the aorta during ventricular diastole utilizing the apparatus and method disclosed herein. The method and apparatus for partially or completely occluding the descending aorta of a patient according to the present invention may be combined with a method of manipulating core and cerebral temperature disclosed in the '776 patent. The protection afforded the invention is intended to be limited only by the scope of the appended claims, as interpreted according to the principles of patent law including the Doctrine of Equivalents.

The embodiments of the invention in which an exclusive property or privilege is claimed are defined as follows:

1. A non-invasive method of subdiaphragm hemorrhage control in a patient, including:
   positioning a moveable surface through the patient's esophagus at a portion of the patient's esophageal-gastric junction that passes through the patient's diaphragm; and
   displacing the esophageal-gastric junction posteriorly with the moveable surface thereby displacing the patient's descending aorta toward the patient's vertebral column as a result of binding of the patient's esophageal-gastric junction and descending aorta at the patient's diaphragm; and
   at least partially occluding the descending aorta between the moveable surface and the patient's vertebral column.

2. The method of claim 1 including positioning said moveable surface with an elongated member and wherein said applying said force includes moving said moveable surface with a displacement mechanism joining said moveable surface to said elongated member.

3. The method of claim 2 including anchoring said elongated member with an anchoring member in the patient's esophagus.

4. The method of claim 2 including anchoring said elongated member with an anchoring member in the patient's stomach.

5. The method of claim 2 wherein said displacement mechanism includes parallel linkages supporting said moveable surface in a parallel relationship with said elongated member.

6. The method of claim 2 wherein said moveable surface pivots with respect to said elongated member.

7. The method of claim 1 wherein said moveable surface is defined by a cuff and wherein said displacing the moveable surface includes inflating said cuff sufficiently to at least partially occlude the descending aorta.

8. The method of claim 7 wherein said cuff inflates unidirectionally.

9. A non-invasive method of enhancing cerebral and myocardial perfusion in a patient, including:

positioning a moveable surface through the patient's esophagus at a portion of the patient's esophageal-gastric junction that passes through the patient's diaphragm; and displacing the esophageal-gastric junction posteriorly with the moveable surface thereby displacing the patient's descending aorta toward the patient's vertebral column as a result of binding of the patient's esophageal-gastric junction and descending aorta at the patient's diaphragm; and at least partially occluding the descending aorta between the moveable surface and the patient's vertebral column and thereby increasing central and intracranial arterial pressure.

10. The method of claim 9 including positioning said moveable surface with an elongated member and wherein said applying said force includes moving said moveable surface with a displacement mechanism joining said moveable surface to said elongated member.

11. The method of claim 10 including anchoring said elongated member with an anchoring member in the patient's esophagus.

12. The method of claim 10 including anchoring said elongated member with an anchoring member in the patient's stomach.

13. The method of claim 10 wherein said displacement mechanism includes parallel linkages supporting said moveable surface in a parallel relationship with said elongated member.

14. The method of claim 10 wherein said moveable surface pivots with respect to said elongated member.

15. The method of claim 9 wherein said moveable surface is defined by a cuff and wherein said displacing the moveable surface includes inflating said cuff sufficiently to at least partially occlude the descending aorta.

16. The method of claim 15 including inflating said cuff unidirectionally.

17. A non-invasive method of enhancing cerebral and myocardial perfusion in a patient, including:

positioning an inflatable device through the patient's esophagus in a portion of the patient's stomach juxtaposed with the patient's descending aorta and at least partially inflating the inflatable device; and applying a force in the patient's stomach with the at least partially inflated device, including applying said force posteriorly in the direction of the patient's descending aorta, said force being sufficient to at least partially occlude the descending aorta and thereby increasing central and intracranial arterial pressure.

18. The method of claim 17 including positioning said inflatable device with an elongated member attached to said inflatable device and wherein said applying said force includes moving said inflatable device in the direction of the patient's diaphragm by applying traction to said elongated member.

19. The method of claim 17 wherein said applying a force includes applying a force on an exterior surface of the patient.

20. The method of claim 19 using a belt around the patient's thoraco-abdominal region to apply said force.

21. The method of claim 17 including positioning said inflatable device with an elongated member and wherein said applying said force includes moving said inflatable device with a connecting member joining said inflatable device to said elongated member.

22. The method of claim 14 wherein said connecting member is a lever.

23. The method of claim 15 including anchoring said elongated member with an anchoring member in the patient's esophagus.

24. The method of claim 21 including anchoring said elongated member with an anchoring member in the patient's stomach.

25. The method of claim 24 wherein said anchoring member is another inflatable device positioned to react with the patient's diaphragm.

26. The method of claim 17 including positioning said inflatable device with an elongated member and wherein said applying a force includes providing a substantially rigid portion of said elongated member and expanding said inflatable device posteriorly from said rigid portion.

27. The method of claim 26 including anchoring said elongated member with an anchoring member in the patient's esophagus.

28. The method of claim 26 including anchoring said elongated member with an anchoring member in the patient's stomach.

29. The method of claim 28 wherein said anchoring member is another inflatable device positioned to react with the patient's diaphragm.

30. The method of claim 29 including defining at least one electrode with at least one of said inflatable devices.

31. The method of claim 17 wherein said applying a force includes inflating said inflatable device posteriorly in the direction of the patient's descending aorta.

32. The method of claim 31 including defining at least one electrode with said inflatable device.

33. The method of claim 17 including applying said force in synchronism with ventricular contractions of the patient.

34. A non-invasive method of subdiaphragm hemorrhage control in a patient, including:

positioning an inflatable device through the patient's esophagus in a portion of the patient's stomach juxtaposed with the patient's descending aorta and at least partially inflating the inflatable device; and applying a force in the patient's stomach with the at least partially inflated device, including applying said force posteriorly in the direction of the patient's descending aorta, said force being sufficient to at least partially occlude the descending aorta.

35. The method of claim 34 including positioning said inflatable device with an elongated member attached to said inflatable device and wherein said applying said force includes moving said inflatable device in the direction of the patient's diaphragm by applying traction to said elongated member.

36. The method of claim 34 wherein said applying a force includes applying a force on an exterior surface of the patient.

37. The method of claim 36 using a belt around the patient's thoraco-abdominal region to apply said force.

38. The method of claim 34 including positioning said inflatable device with an elongated member and wherein said applying said force includes moving said inflatable device with a connecting member joining said inflatable device to said elongated member.

39. The method of claim 38 wherein said connecting member is a lever.

40. The method of claim 39 including anchoring said elongated member with an anchoring member in the patient's esophagus.

41. The method of claim 38 including anchoring said elongated member with an anchoring member in the patient's stomach.

42. The method of claim 41 wherein said anchoring member is another inflatable device positioned to react with the patient's diaphragm.

43. The method of claim 42 including defining at least one electrode with at least one of said inflatable devices.

44. The method of claim 34 including positioning said inflatable device with an elongated member and wherein said applying a force includes providing a substantially rigid portion of said elongated member and expanding said inflatable device posteriorly from said rigid portion.

45. The method of claim 44 including anchoring said elongated member with an anchoring member in the patient's esophagus.

46. The method of claim 44 including anchoring said elongated member with an anchoring member in the patient's stomach.

47. The method of claim 46 wherein said anchoring member is another inflatable device positioned to react with the patient's diaphragm.

48. The method of claim 47 including defining at least one electrode with at least one of said inflatable devices.

49. The method of claim 34 wherein said applying a force includes inflating said inflatable device posteriorly in the direction of the patient's descending aorta.

50. The method of claim 34 including defining at least one electrode with said inflatable device.

51. The method of claim 34 including applying said force in synchronism with ventricular contractions of the patient.

* * * * *